(12) United States Patent
Cao et al.

(10) Patent No.: US 10,843,980 B2
(45) Date of Patent: *Nov. 24, 2020

(54) MANUFACTURING A BASE STOCK FROM ETHANOL

(71) Applicant: ExxonMobil Research and Engineering Company, Annandale, NJ (US)

(72) Inventors: Guang Cao, Princeton, NJ (US); Suzzy C. Ho, Princeton, NJ (US); Matthew S. Ide, Doylestown, PA (US); Shifang L. Luo, Annandale, NJ (US); William R. Gunther, Clinton, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/541,539

(22) Filed: Aug. 15, 2019

(65) Prior Publication Data

US 2020/0062674 A1 Feb. 27, 2020

Related U.S. Application Data

(60) Provisional application No. 62/721,246, filed on Aug. 22, 2018.

(51) Int. Cl.
*C07C 2/32* (2006.01)
*B01J 31/18* (2006.01)
(Continued)

(52) U.S. Cl.
CPC ............. *C07C 2/32* (2013.01); *B01J 31/1815* (2013.01); *C07C 1/24* (2013.01); *C07C 4/02* (2013.01); *C07C 7/04* (2013.01); *C07C 11/04* (2013.01)

(58) Field of Classification Search
CPC .... C07C 2/32; C07C 1/24; C07C 4/02; C07C 7/04; C07C 11/04; B01J 31/143;
(Continued)

(56) References Cited

U.S. PATENT DOCUMENTS 4,153,638 A    5/1979  Bercik et al.
4,390,413 A *  6/1983  O'Rear .................... B01J 29/40
                                                       208/100
(Continued)

FOREIGN PATENT DOCUMENTS

DE    102006039904 A1    2/2008
EP        276096 A1      7/1988
(Continued)

OTHER PUBLICATIONS

Nuroil (attached document; available on Jun. 13, 2015; https://web.archive.org/web/20150601000000*/http://www.nuroil.com/baseoil.aspx) (Year: 2015).*

(Continued)

*Primary Examiner* — In Suk C Bullock
*Assistant Examiner* — Jason Y Chong
(74) *Attorney, Agent, or Firm* — Scott F. Yarnell

(57) ABSTRACT

Methods and a system for manufacturing a base stock from an ethanol stream are provided. An example method includes dehydrating an ethanol stream to form an impure ethylene stream, recovering an ethylene stream from the impure ethylene stream, and oligomerizing the ethylene stream to form a raw oligomer stream. A light olefinic stream is distilled from the raw oligomer stream and blended with the ethylene stream prior to the oligomerization. A heavy olefinic stream is distilled from the raw oligomer stream and hydro-processed to form a hydro-processed stream. The hydro-processed stream is distilled to form the base stock.

9 Claims, 10 Drawing Sheets

(51) Int. Cl.
*C07C 7/04* (2006.01)
*C07C 4/02* (2006.01)
*C07C 1/24* (2006.01)
*C07C 11/04* (2006.01)

(58) Field of Classification Search
CPC ............ B01J 31/1815; B01J 2531/0244; B01J 2531/842; B01J 2231/20; B01J 29/703; B01J 2540/22; C10G 2300/4081; C10G 3/45; C10G 3/49; C10G 69/06; C10G 69/123; C10G 69/126; C10G 29/205; C10G 3/57; C10G 50/02
See application file for complete search history.

(56) References Cited

U.S. PATENT DOCUMENTS

| | | | |
|---|---|---|---|
| 4,417,082 A | 11/1983 | Larkin et al. | |
| 4,467,128 A * | 8/1984 | Vora | C07C 2/70 585/456 |
| 4,551,438 A | 11/1985 | Miller | |
| 4,855,526 A | 8/1989 | Hen | |
| 4,897,245 A | 1/1990 | Hsia et al. | |
| 4,899,014 A | 2/1990 | Avidan et al. | |
| 4,899,015 A | 2/1990 | Harandi et al. | |
| 4,942,021 A | 7/1990 | Garwood et al. | |
| 4,956,514 A | 9/1990 | Chu | |
| 4,973,790 A | 11/1990 | Beech, Jr. et al. | |
| 5,004,852 A | 4/1991 | Harandi | |
| 5,019,357 A | 5/1991 | Harandi et al. | |
| 5,321,190 A | 6/1994 | Aufdembrink et al. | |
| 5,960,643 A | 10/1999 | Kuechler et al. | |
| 6,111,156 A | 8/2000 | Oballa et al. | |
| 6,124,513 A | 9/2000 | Heilman et al. | |
| 6,212,905 B1 | 4/2001 | Kuechler et al. | |
| 6,262,324 B1 | 7/2001 | Heilmann et al. | |
| 6,388,148 B2 | 5/2002 | Heilmann et al. | |
| 6,417,416 B1 | 7/2002 | Heilman et al. | |
| 6,441,263 B1 | 8/2002 | O'Rear et al. | |
| 6,586,646 B1 | 7/2003 | Heilman et al. | |
| 6,660,894 B1 | 12/2003 | Wu et al. | |
| 6,730,818 B2 | 5/2004 | Heilman et al. | |
| 6,911,410 B2 | 6/2005 | Lecocq et al. | |
| 6,951,831 B2 | 10/2005 | Lecocq et al. | |
| 7,314,964 B2 | 1/2008 | Abrevaya et al. | |
| 7,972,498 B2 | 7/2011 | Buchanan et al. | |
| 7,989,668 B2 | 8/2011 | Godsmark et al. | |
| 8,137,533 B2 | 3/2012 | Towler et al. | |
| 8,173,855 B2 | 5/2012 | Kotter et al. | |
| 8,237,004 B2 * | 8/2012 | Timken | C10G 50/00 585/800 |
| 8,481,451 B2 | 7/2013 | Kang et al. | |
| 8,784,743 B2 | 7/2014 | Keusenkothen et al. | |
| 2003/0220191 A1 | 11/2003 | Lecocq et al. | |
| 2005/0101814 A1 | 5/2005 | Foley et al. | |
| 2006/0173230 A1 | 8/2006 | Chang et al. | |
| 2007/0090018 A1 | 4/2007 | Keusenkothen et al. | |
| 2007/0090019 A1 | 4/2007 | Keusenkothen et al. | |
| 2007/0112089 A1 | 5/2007 | Boelt et al. | |
| 2007/0142684 A1 * | 6/2007 | Elomari | C10M 177/00 585/332 |
| 2010/0048968 A1 | 2/2010 | Lauritzen et al. | |
| 2012/0071701 A1 | 3/2012 | Glover | |
| 2012/0125811 A1 | 5/2012 | Bridges et al. | |
| 2013/0158321 A1 | 6/2013 | Olivier-Bourbigou et al. | |
| 2014/0275669 A1 | 9/2014 | Daage et al. | |
| 2015/0218065 A1 | 8/2015 | Fritz et al. | |
| 2016/0168491 A1 | 6/2016 | Yao et al. | |
| 2016/0194572 A1 * | 7/2016 | Lilga | C07C 2/66 585/14 |
| 2017/0369804 A1 | 12/2017 | Lilga et al. | |

FOREIGN PATENT DOCUMENTS

| | | |
|---|---|---|
| EP | 2228355 A1 | 9/2010 |
| EP | 2970043 A1 | 1/2016 |
| GB | 2435883 A | 9/2007 |
| KR | 10-1568859 B1 | 11/2015 |
| WO | 2011138520 A2 | 11/2011 |
| WO | 2011156892 A2 | 12/2011 |
| WO | 2014154799 A1 | 10/2014 |

OTHER PUBLICATIONS

Small et al. ("Iron-Based Catalysts with Exceptionally High Activities and Selectivities for Oligomerization of Ethylene to Linear α-Olefins", J. Am. Chem. Soc. 1998, 120, 7143-7144). (Year: 1998).*

The International Search Report and Written Opinion of PCT/US2019/046641 dated Nov. 28, 2019.

The International Search Report and Written Opinion of PCT/US2019/046606 dated Nov. 22, 2019.

The International Search Report and Written Opinion of PCT/US2019/046696 dated Nov. 22, 2019.

Small et al., "Iron-based catalysts with exceptionally high activities and selectivities for oligomerization of ethylene to linear alpha-olefins", J. Am. Chem. Soc. 120 (1998), pp. 7143-7144.

* cited by examiner

108

400

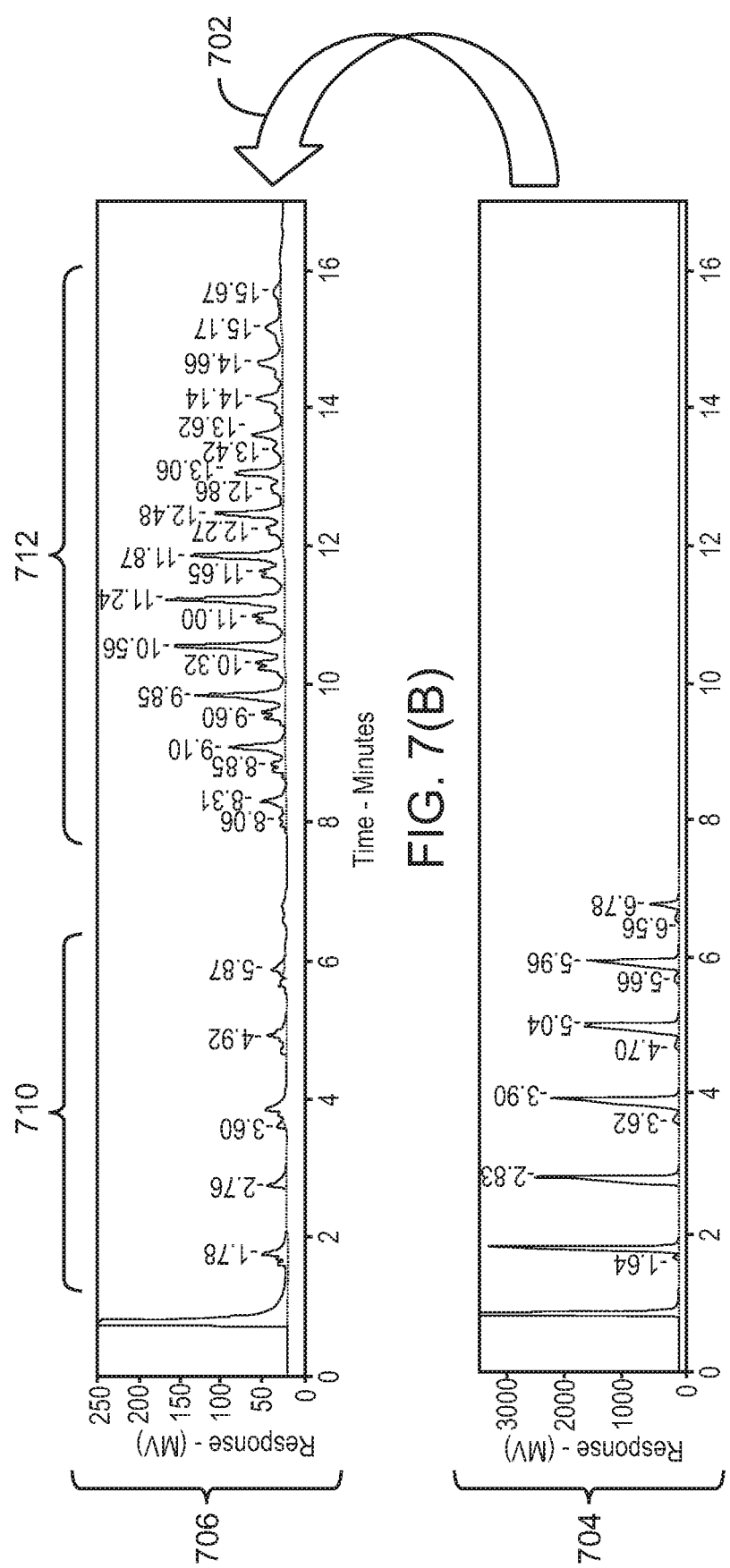

MANUFACTURING A BASE STOCK FROM ETHANOL

CROSS-REFERENCE TO RELATED APPLICATIONS

This application claims the benefit of U.S. Provisional Application No. 62/721,246, filed on Aug. 22, 2018, the entire contents of which are incorporated herein by reference.

FIELD

The techniques described herein provide systems and methods for manufacturing a lubricant base stock from ethanol. The ethanol is dehydrated to generate an ethylene stream that is oligomerized and hydro-processed to form the base stock.

BACKGROUND

This section is intended to introduce various aspects of the art, which may be associated with examples of the present techniques. This description is believed to assist in providing a framework to facilitate a better understanding of particular aspects of the present techniques. Accordingly, it should be understood that this section should be read in this light, and not necessarily as admissions of prior art.

High molecular weight paraffins suitable for the production of high quality lube base stock and distillate fuel may be in short supply and expensive to manufacture. In addition, the oligomerization of olefins is typically performed with high purity feed streams, such as polymer grade ethylene.

The production of higher molecular weight linear paraffins and isoparaffins, for example, to form base stocks, from hydrocarbon streams may involve numerous steps, which affect the costs for the final products. One example of the production of these compounds is the production of syngas, CO and $H_2$ by steam reforming of methane, followed by methanol synthesis. The methanol may then be converted to olefins via a methane-to-olefins (MTO) process. The olefins are further oligomerized to higher molecular weight hydrocarbons. In another example, syngas is produced for use in Fischer-Tropsch reactions which preferentially synthesize linear high molecular weight products. However, these options may be economically problematic due to the need to first produce syngas.

Some previous research activities have focused on using impure ethylene feeds to produce polyalphaolefins (PAOs). For example, U.S. Patent Application Publication No. 2010/0249474 by Nicholas et al. discloses a "process for oligomerizing dilute ethylene." As described in the publication, a fluid catalytic process (FCC) may provide a dilute ethylene stream, as heavier hydrocarbons are processed. The ethylene in the dilute ethylene stream may be oligomerized using a catalyst, such as an amorphous silica-alumina base with a Group VIII or VIB metal that is resistant to feed impurities such as hydrogen sulfide, carbon oxides, hydrogen and ammonia. About 40 wt. %, or greater, of the ethylene in the dilute ethylene stream can be converted to heavier hydrocarbons.

Further, U.S. Patent Application Publication No. 2014/0275669 by Daage, et al, discloses the "production of lubricant base oils from dilute ethylene feeds." As described in this publication, a dilute ethylene feed, for example, formed while cracking heavier hydrocarbons, may be oligomerized to form oligomers for use as fuels or lubricant base oils. The oligomerization of the impure dilute ethylene is performed with a zeolitic catalyst. The zeolitic catalyst is resistant to the presence of poisons such as sulfur and nitrogen in the ethylene feed. Diluents such as light paraffins, may be present without interfering with the process.

The feed used for both processes described above is derived from the processing of oil in a fluid catalytic cracker (FCC). In an FCC, heavier hydrocarbons, such as crude oil fractions with a molecular weight of about 300 to about 600, or higher, are contacted with a catalyst at high temperatures to form lower molecular weight compounds. The byproduct gases from the FCC include olefins that may be used to form the oligomers.

The oligomerization of blends of ethylene with co-monomers, such as 1-hexene, 1-heptene, 1-octene, 1-dodecene, and 1-hexadecene, has been explored. For example, U.S. Pat. No. 7,238,764 describes a process for the co-oligomerization of ethylene and alpha olefins. The co-oligomerization of the alpha olefins with ethylene is performed in the presence of a metal catalyst system. The metal catalyst system may include bis-aryliminepyridine MXa complexes, [bis-aryliminepyridine $MY_p.L_b^+][NC^-]_q$ complexes, or both. The process is carried out in an ethylene pressure of less than about 2.5 megapascals (MPa).

SUMMARY

In an embodiment, the present invention provides a system for manufacturing a base stock from an ethanol stream. The system includes a dehydration reactor configured to form an impure ethylene stream from the ethanol stream, a recovery system configured to purify the impure ethylene stream to form an ethylene stream, and an oligomerization reactor configured to oligomerize the ethylene stream to form a raw oligomer stream. A distillation column is configured to separate a light olefinic stream from the raw oligomer stream, wherein the light olefinic stream is blended with the ethylene stream to form a blended stream, and the blended stream is provided to the oligomerization reactor. The distillation column is also configured to separate an intermediate olefinic stream, and a heavy olefinic stream from the raw oligomer stream. A hydro-processing system is configured to hydroprocess the heavy olefinic stream to form a hydroprocessed stream. A product distillation column is configured to separate the hydroprocessed stream to form the base stock.

In another embodiment, the present invention provides a method for manufacturing a base stock from an ethanol stream. The method includes dehydrating an ethanol stream to form an impure ethylene stream, recovering an ethylene stream from the impure ethylene stream, and oligomerizing the ethylene stream to form a raw oligomer stream. A light olefinic stream is distilled from the raw oligomer stream and blended into the ethylene stream prior to the oligomerization. A heavy olefinic stream is distilled from the raw oligomer stream, and hydro-processed to form a hydroprocessed stream. The hydroprocessed stream is distilled to form the base stock.

In another embodiment, the present invention discloses a system for manufacturing a base oil stock from ethanol. The system includes a dehydration reactor configured to form an impure ethylene stream from an ethanol stream. A recovery system is configured to form an ethylene stream from the impure ethylene stream. An oligomerization reactor is configured to convert the ethylene stream to a raw olefinic stream by contacting the ethylene stream with a homogeneous catalyst. A distillation column is configured to separate a light olefinic stream and a heavy olefinic stream from the raw olefinic stream and the light olefinic stream is combined with the ethylene stream to the oligomerization reactor. A hydro-processing system is configured to hydroprocess the heavy olefinic stream to form a hydroprocessed stream. The hydroprocessed stream may be demetallated, hydrocracked, or hydroisomerized, or any combination thereof.

DESCRIPTION OF THE DRAWINGS

The advantages of the present techniques are better understood by referring to the following detailed description and the attached drawings.

FIGS. 7(A) and 7(B) are plots of gas chromatograms illustrating the changes caused by dimerization of an alpha olefin mixture, in accordance with examples.

DETAILED DESCRIPTION

In the following detailed description section, specific examples of the present techniques are described. However, to the extent that the following description is specific to a particular example or a particular use of the present techniques, this is intended to be for exemplary purposes only and simply provides a description of the exemplary examples. Accordingly, the techniques are not limited to the specific examples described below, but rather, include all alternatives, modifications, and equivalents falling within the true spirit and scope of the appended claims.

Figure 4:
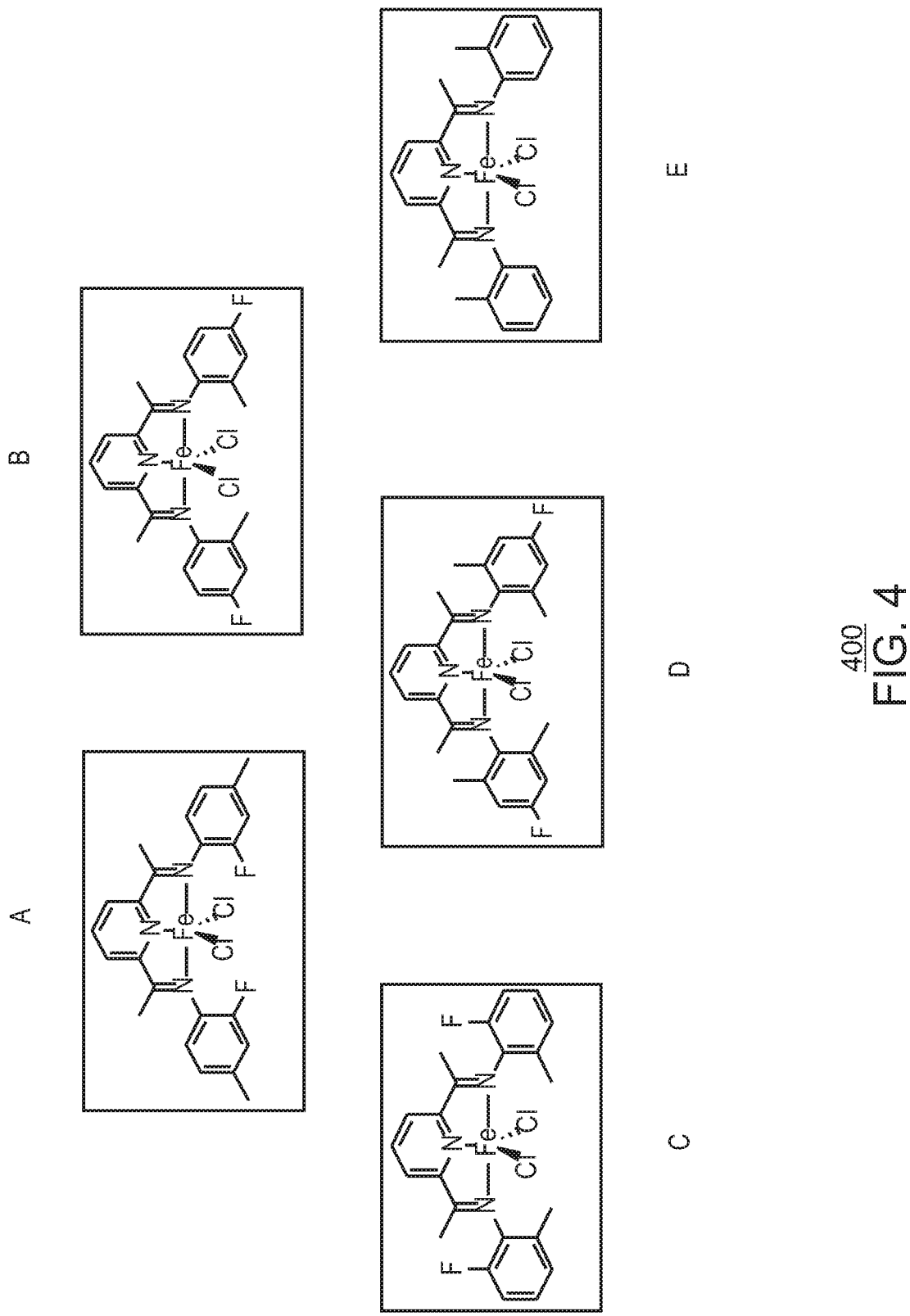
FIG. 4 is a drawing of related homogeneous catalysts, having different ligands, that may be used for the oligomerization or dimerization processes, in accordance with examples.

As renewable feedstock becomes more abundant the biological production of ethanol, termed bioethanol herein, may provide a significant source of feedstocks for hydrocarbon products. The process described herein allows the coproduction of high quality (Group III) base stock and linear alpha olefins from a renewable feedstock, such as bioethanol. The process begins with the production of ethylene from bioethanol through catalytic dehydration. The ethylene is purified, for example to remove the water from the dehydration, among other contaminants. The purified ethylene stream is then introduced to a reaction zone in an oligomerization reactor where a homogeneous catalyst, for example, as described with respect to FIG. 4, is used to generate linear alpha-olefins (LAOS) with a Schulz-Flory (S-F) distribution.

As used herein, a "catalyst" is a material that increases the rate of specific chemical reactions under certain conditions of temperature and pressure. Catalysts may be heterogeneous, homogenous, and bound. A heterogeneous catalyst is a catalyst that has a different phase from the reactants. The phase difference may be in the form of a solid catalyst with liquid or gaseous reactants or in the form of immiscible phases, such as an aqueous acidic catalyst suspended in droplets in an organic phase holding the reactants. A heterogeneous catalyst may be bound, such as a zeolite bound with alumina or another metal oxide. A homogeneous catalyst is soluble in the same phase as the reactants, such as an organometallic catalyst dissolved in an organic solvent with a reactant.

As used herein, "base stock" or "base oil stock" refers to hydrocarbons that may include paraffins, isoparaffins, napthenes, and aromatic compounds in the lubricant range of molecular weights. The base stocks may include semi-synthetic or synthetic feedstocks such as linear paraffins and isoparaffins in a lubricant range of molecular weights, in addition to highly branched molecules useful for chemical applications, such as hydrocarbon fluids. Group I base stocks or base oils are defined as base oils with less than 90 wt. % saturated molecules and/or at least 0.03 wt. % sulfur content. Group I base stocks also have a viscosity index (VI) of at least 80 but less than 120. Group II base stocks or base oils contain at least 90 wt. % saturated molecules and less than 0.03 wt. % sulfur. Group II base stocks also have a viscosity index of at least 80 but less than 120. Group III base stocks or base oils contain at least 90 wt. % saturated molecules and less than 0.03 wt. % sulfur, with a viscosity index of at least 120. Other hydrocarbons that may be produced with base stocks include gasoline, diesel fuels, distillates, and other hydrocarbon fluids.

Further, the base stocks may be referred to as light neutral (LN), medium neutral (MN), and heavy neutral (HN), for example, as determined by viscosity. The term "neutral" generally indicates the removal of most nitrogen and sulfur atoms to lower reactivity in the final oil. The base stocks are generally classified by viscosity, measured at 100° C. as a kinematic viscosity under the techniques described in ASTM D445. The viscosity may be reported in millimeters^2/second (centistokes, cSt). The base stocks may also be classified by boiling point range, for example, determined by simulated distillation on a gas chromatograph, under the techniques described in ASTM D 2887. It should be noted that the viscosity ranges and boiling point ranges described herein are merely examples, and may change, depending on the content of linear paraffins, branched paraffins, cyclic hydrocarbons, and the like. A light neutral base stock may have a kinematic viscosity of about 4 cSt to about 6 cSt and may have a boiling point range of about 380° C. to about 450° C. A medium neutral base stock may have a kinematic viscosity of about 6 cSt to about 10 cSt and a boiling point range of about 440° C. to about 480° C. A heavy neutral base stock may have a kinematic viscosity of about 10 cSt to about 20 cSt, or higher, and a boiling point range of about 450° C. to about 565° C.

The oligomerization reaction forms oligomers by reacting small molecule olefins, such as ethylene and propylene, termed monomers, to form a short chain or oligomer. The oligomers may include two to 50 monomers, or more, depending on the reaction conditions used. The oligomers may be linear alpha-olefins with a Schulz-Flory (S-F) distribution. As used herein, an S-F distribution is a probability distribution that describes the relative ratios of oligomers of different lengths that occur in an ideal step-growth oligomerization process. Generally, shorter oligomers are favored over longer oligomers.

However, the S-F distribution of the olefinic products may be controlled by the selection of an organic ligand on the catalyst, or through the selection of reaction conditions such as temperature and pressure. These choices may be used to enhance the production of either light LAOs or heavier, base stock range molecules. The product olefins may then be split into light olefinic (C12−), medium olefinic (C12-C22), and heavy olefinic (C24+) fractions, for example, through conventional distillation. It may be noted that the olefinic fractions may not be pure olefins, but may include other compounds with similar boiling points, such as paraffinic compounds. The light fraction may include C4, C6, C8, C10, and C12 LAOS, the medium fraction may be sent to a dimerization or alkylation reactor using a catalyst selected from a variety of heterogeneous or homogeneous catalysts, and the heavy fraction may be sent to a demetallation zone or stage then to a hydrocracking/hydroisomerization (HDC/HDI) reactor to produce the high quality (Group III) base stock.

The ability to control the S-F distribution makes the targeted production of particular products possible. In some examples, an S-F distribution of about 0.75 to about 0.91 is targeted to make various wax and base stock products with carbon numbers of at least 24. In other examples, an S-F distribution of about 0.83 to about 0.87 is targeted to make products having about 24 to about 50 carbon atoms, such as lower viscosity base stocks. In further examples, an S-F distribution of about 0.6 to about 0.75 is targeted to make products having about four to about 22 carbon atoms, such as various linear alpha olefins. The relation of S-F distribution to various carbon numbers is discussed with respect to FIG. 6.

For ease of reference, certain terms used in this application and their meanings as used herein are set forth. To the extent a term is not defined herein, it should be given the broadest definition persons in the pertinent art have given that term as reflected in at least one printed publication or issued patent. Further, the present techniques are not limited by the usage of the terms shown herein, as all equivalents, synonyms, new developments, and terms or techniques that serve the same or a similar purpose are considered to be within the scope of the present claims.

Figure 1A:
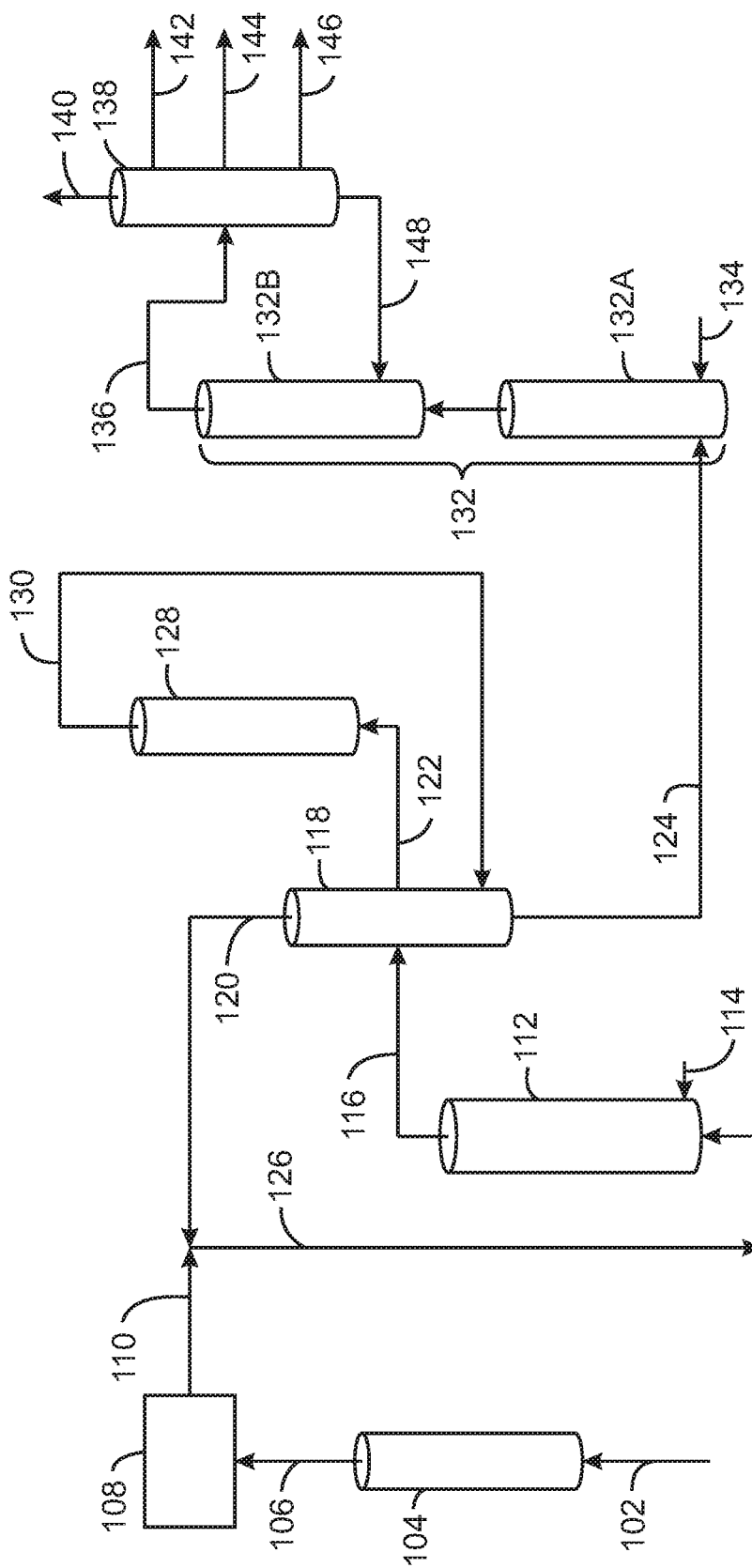
FIG. 1(A) is a simplified block diagram of a system for producing base stocks from an ethanol feed, in accordance with examples.

FIG. 1(A) is a simplified block diagram of a system 100 for producing base stocks from an ethanol feed, in accordance with examples. The process begins with the introduction of the ethanol feed stream 102 to a dehydration reactor 104. As sourced from a fermentation process and purified by distillation, the ethanol feed stream 102 may contain 4.6 wt. % water as an azeotropic mixture. Depending on the process used to produce the ethanol feed stream 102, other treatments may be used for purification including, for example, filtration, distillation, membrane purification, and the like.

Dehydration

In the dehydration reactor 104, the ethanol feed stream 102 may be vaporized and contacted with a solid acid catalyst, such as γ-Al2O3 based, molecular sieve (HZSM-5 zeolites), and heteropoly acid, at 150–500° C. and 1-50 bar pressure. These catalysts can be modified with other metal oxides (e.g., MgO/SiO2) and doped with chemical elements (e.g., La/P), resulting in varying lifetime, conversion of ethanol, and selectivity for ethylene to form a raw ethylene stream 106. The mixture of products in the raw ethylene stream 106 from the dehydration reactor 104 may include ethylene, water, diethylether, and small amounts of other materials, for example, acetaldehyde, hydrogen and light hydrocarbons.

A separation system 108 may be used to separate the water formed in the dehydration process from the raw ethylene stream 106 to form an oligomerization feed stream 110. The separation system 108 may include a condenser to remove water, as described with respect to FIG. 1(B), a caustic column, or a dryer, forming the oligomerization feed stream 110. After water removal, the oligomerization feed stream 110 may include, for example, about 95% ethylene, about 99% ethylene, or higher, the impurities being hydrogen, methane, ethane, or propane.

Oligomerization

The oligomerization feed stream 110 is provided to an oligomerization reactor 112, where it may be contacted with a homogenous catalyst 114, for example, an organometallic catalyst. In examples described herein, the homogenous catalyst 114 is generally an impurity tolerant homogeneous catalyst, such as an Iron (II) pyridine-bis-imide (Fe—PBI), capable of the oligomerization of the oligomerization feed stream 110 to C10+ products, C25+, or C50+ products, to produce diesel, lube, and hydrocarbon fluid molecules, such as the base stocks.

An example of a homogenous catalyst that may be includes an iron (II) pyridine-bis-imine (Fe—PBI) compound having a structure of formula 1:

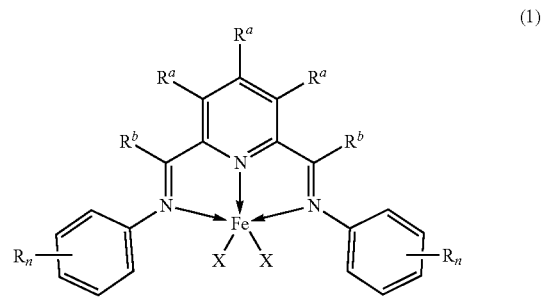

(1)

In formula 1, X is a halogen or hydrocarbyl radical, such as Cl. Each R substituent is independently a halogen or hydrocarbyl radical, and each n is an integer from 1-5 representing the number of R groups present. Each n is 1, 2 or 3. In some examples, n is 2 or 3. Each R is a C1-C10 alkyl, or a halogen. In some examples, R is methyl, ethyl or n-propyl. In some examples, at least one R is methyl. In some examples, at least one R is fluorine. In some examples, Rn comprises one, two, or three substituents, wherein each of the substituents is methyl, or fluorine. Each $R^a$, and $R^b$ are independently a hydrogen, halogen or hydrocarbyl radical. In some examples, each $R^a$ is a hydrocarbyl or hydrogen, or a hydrogen. Each $R^b$ is a hydrocarbyl, such as a C1-C10 alkyl, or methyl.

The homogenous catalyst may include an iron (II) pyridine-bis-imine (Fe—PBI) compound having a structure of formula 2:

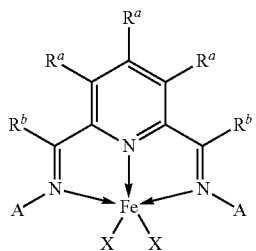
(2)

In formula 2, each $R^a$, $R^b$ and X are as defined above, and each A is independently a substituted aryl group including one, two or three R substituents as defined above.

In some examples, each A is defined by a structure shown in formula 3:

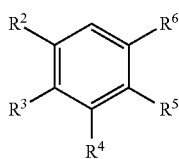
(3)

In formula 3, the one position of the phenyl ring is bonded to the nitrogen of the iron (II) pyridine-bis-imine complex, and each $R^2$, $R^3$, $R^4$, $R^5$, and $R^6$ are independently C1 to C10 alkyl, halogen or hydrogen radical. In some examples, each $R^2$, $R^3$, $R^4$, $R^5$, and $R^6$ are independently methyl, ethyl, n-propyl, fluoro, and hydrogen. In some examples, each $R^2$, $R^3$, $R^4$, $R^5$, and $R^6$ are independently methyl, fluoro and hydrogen. In some examples, each $R^2$ is methyl and each $R^6$ is fluoro. In some examples, each $R^2$ is fluoro and each $R^4$ is methyl. In some examples, each $R^2$ and $R^6$ are methyl, and each $R^4$ is fluoro. In some examples, each $R^2$ is methyl and each $R^4$ is fluoro. In some examples, each $R^2$ is methyl. Examples of homogeneous catalysts that may be used for the oligomerization are discussed further with respect to FIG. 4. In some examples, the organometallic catalysts may be supported to form heterogeneous catalysts.

Generally, the homogeneous catalysts are activated. After the complexes have been synthesized, catalyst systems may be formed by combining them with activators in any manner known from the literature, including by supporting them for use in slurry or gas phase polymerization reactions. The catalyst systems may also be added to or generated in solution polymerization or bulk polymerization (in the monomer). The catalyst system typically includes a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle, typically in a 10 wt. % solution in toluene. In some embodiments, the catalyst system uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; or from 1:2000 to 10:1; or from 1:1000 to 10:1; or from 1:500 to 1:1; or from 1:300 to 1:1; or from 1:200 to 1:1; or from 1:100 to 1:1; or from 1:50 to 1:1; or from 1:10 to 1:1. When the activator is an alumoxane (modified or unmodified), some examples select the maximum amount of activator at a 5000-fold molar excess over the catalyst precursor (per metal catalytic site). The preferred minimum activator-to-complex ratio is 1:1 molar ratio.

Activation may also be performed using non-coordinating anions, (NCAs), of the type described in European Patent Application Nos. 277 003 A1 and 277 004 A1. An NCA may be added in the form of an ion pair using, for example, [DMAH]+[NCA]− in which the N,N-dimethylanilinium (DMAH) cation reacts with a basic leaving group on the transition metal complex to form a transition metal complex cation and [NCA]−. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis (pentafluorophenyl)borate (i.e., [PhNMe$_2$H]B(C$_6$F$_5$)$_4$) and N,N-dimethylanilinium tetrakis (heptafluoronaphthyl)borate, where Ph is phenyl, and Me is methyl.

Additionally, activators useful herein include those described in U.S. Pat. No. 7,247,687 at column 169, line 50 to column 174, line 43, particularly column 172, line 24 to column 173, line 53. These are incorporated by reference herein.

Non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion.

The term NCA also includes neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

In an example described herein, the non-coordinating anion activator is represented by the following formula (1):

$$(Z)_d^+ (A^{d-}) \quad (1)$$

wherein Z is (L-H) or a reducible Lewis acid; L is a neutral Lewis base; H is hydrogen and (L-H)$^+$ is a Bronsted acid; $A^{d-}$ is a non-coordinating anion having the charge d−; and d is an integer from 1 to 3.

When Z is (L-H) such that the cation component is (L-H)d+, the cation component may include Bronsted acids such as protonated Lewis bases capable of protonating a moiety, such as an alkyl or aryl, from the catalyst precursor, resulting in a cationic transition metal species, or the activating cation (L-H)d+ is a Bronsted acid, capable of donating a proton to the catalyst precursor resulting in a transition metal cation, including ammoniums, oxoniums, phosphoniums, siliyums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, it may be represented by the formula: ($Ar_3C+$), where Ar is aryl or aryl substituted with a heteroatom, or a $C_1$ to $C_{40}$ hydrocarbyl, the reducible Lewis acid may be represented by the formula: ($Ph_3C+$), where Ph is phenyl or phenyl substituted with a heteroatom, and/or a C1 to C40 hydrocarbyl. In an example, the reducible Lewis acid is triphenyl carbenium.

Examples of the anion component Ad– include those having the formula [Mk+Qn]d– wherein k is 1, 2, or 3; n is 1, 2, 3, 4, 5 or 6, or 3, 4, 5 or 6; n-k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, said Q having up to about 20 carbon atoms with the proviso that in not more than one occurrence is Q a halide, and two Q groups may form a ring structure. Each Q may be a fluorinated hydrocarbyl radical having about 1 to 20 carbon atoms, or each Q is a fluorinated aryl radical, or each Q is a pentafluoryl aryl radical. Examples of suitable Ad– components also include diboron compounds as disclosed in U.S. Pat. No. 5,447,895, which is fully incorporated herein by reference.

In an example in any of the NCAs represented by Formula 1 described above, the anion component Ad– is represented by the formula [M*k*+Q*n*]d*– wherein k* is 1, 2, or 3; n* is 1, 2, 3, 4, 5, or 6 (or 1, 2, 3, or 4); n*-k*=d*; M* is boron; and Q* is independently selected from hydride, bridged or unbridged dialkylamido, halogen, alkoxide, aryloxide, hydrocarbyl radicals, said Q* having up to about 20 carbon atoms with the proviso that in not more than 1 occurrence is Q* a halogen.

The techniques describe herein also relate method to dimerize olefins including contacting olefins (such as ethylene, butene, hexane, and others) with a catalyst complex as described above and an NCA activator represented by the Formula (2):

$$R_nM**(ArNHal)_{4-n} \quad (2)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA including an anion of Formula 2 also includes a suitable cation that is essentially non-interfering with the ionic catalyst complexes formed with the transition metal compounds, or the cation is $Z_d^+$ as described above.

In an example, in any of the NCAs including an anion represented by Formula 2 described above, R is selected from the group consisting of $C_1$ to $C_{30}$ hydrocarbyl radicals. In an example, $C_1$ to $C_{30}$ hydrocarbyl radicals may be substituted with one or more $C_1$ to $C_{20}$ hydrocarbyl radicals, halide, hydrocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl radicals; —SRa, —NR$^a_2$, and —PR$^a_2$, where each R$^a$ is independently a monovalent $C_4$ to $C_{20}$ hydrocarbyl radical including a molecular volume greater than or equal to the molecular volume of an isopropyl substitution or a $C_4$ to $C_{20}$ hydrocarbyl substituted organometalloid having a molecular volume greater than or equal to the molecular volume of an isopropyl substitution.

In an example, in any of the NCAs including an anion represented by Formula 2 described above, the NCA also includes cation including a reducible Lewis acid represented by the formula: ($Ar_3C+$), where Ar is aryl or aryl substituted with a heteroatom, and/or a $C_1$ to $C_{40}$ hydrocarbyl, or the reducible Lewis acid represented by the formula: ($Ph_3C+$), where Ph is phenyl or phenyl substituted with one or more heteroatoms, and/or $C_1$ to $C_{40}$ hydrocarbyls.

In an example in any of the NCAs including an anion represented by Formula 2 described above, the NCA may also include a cation represented by the formula, (L-H)d+, wherein L is an neutral Lewis base; H is hydrogen; (L-H) is a Bronsted acid; and d is 1, 2, or 3, or (L-H)d+ is a Bronsted acid selected from ammoniums, oxoniums, phosphoniums, silyliums, and mixtures thereof.

Further examples of useful activators include those disclosed in U.S. Pat. Nos. 7,297,653 and 7,799,879, which are fully incorporated by reference herein.

In an example, an activator useful herein includes a salt of a cationic oxidizing agent and a non-coordinating, compatible anion represented by the Formula (3):

$$(OX^{e+})_d(A^{d-})_e \quad (3)$$

wherein $OX^{e+}$ is a cationic oxidizing agent having a charge of e+; e is 1, 2 or 3; d is 1, 2 or 3; and $A^{d-}$ is a non-coordinating anion having the charge of d–(as further described above). Examples of cationic oxidizing agents include: ferrocenium, hydrocarbyl-substituted ferrocenium, $Ag^+$, or $Pb^{+2}$. Suitable examples of $A^{d-}$ include tetrakis(pentafluorophenyl)borate.

Activators useful in catalyst systems herein include: trimethylammonium tetrakis(perfluoronaphthyl)borate, N,N-dimethylanilinium tetrakis(perfluoronaphthyl) borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated by reference herein.

Suitable activators also include: N,N-dimethylanilinium tetrakis (perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph3C+][B(C6F5)4–], [Me3NH+][B(C6F5)4–]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In an example, the activator includes a triaryl carbonium (such as triphenylcarbenium tetraphenylborate, triphenylcarbenium tetrakis(pentafluorophenyl) borate, triphenylcarbenium tetrakis-(2,3,4,6-tetrafluorophenyl)borate, triphenyl carbenium tetrakis(perfluoronaphthyl)borate, triphenylcarbenium tetrakis(perfluorobiphenyl)borate, triphenylcarbenium tetrakis(3,5-bis(trifluoromethyl) phenyl)borate).

In an example, two NCA activators may be used in the polymerization and the molar ratio of the first NCA activator to the second NCA activator can be any ratio. In an example, the molar ratio of the first NCA activator to the second NCA activator is 0.01:1 to 10,000:1, or 0.1:1 to 1000:1, or 1:1 to 100:1.

In an example, the NCA activator-to-catalyst ratio is a 1:1 molar ratio, or 0.1:1 to 100:1, or 0.5:1 to 200:1, or 1:1 to 500:1 or 1:1 to 1000:1. In an example, the NCA activator-to-catalyst ratio is 0.5:1 to 10:1, or 1:1 to 5:1.

In an example, the catalyst compounds can be combined with combinations of alumoxanes and NCAs (see for example, U.S. Pat. Nos. 5,153,157; 5,453,410; European Patent Application No. EP 0 573 120 B1; WIPO Patent Publication No. WO 94/07928; and WIPO Patent Publication No. WO 95/14044 which discuss the use of an alumoxane in combination with an ionizing activator, all of which are incorporated by reference herein).

In an example, when an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately, a co-activator or chain transfer agent, such as a group 1, 2, or 13 organometallic species (e.g., an alkyl aluminum compound such as tri-n-octyl aluminum), may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

When the catalyst compounds are ligated metal dihalide compounds, a co-activator is always used when an NCA activator is used.

Other catalysts, including heterogeneous catalyst such as zeolites, may be used for the oligomerization. However, the oligomerization process may not be as clean, e.g., producing more isomers and fewer linear alpha olefins. Zeolites that may be suitable for this conversion include, but are not limited to 10-ring zeolites such as ZSM-5 (MFI), ZSM-11 (MEL), ZSM-48 (MRE), and the like, with $Si/Al_2$ ratios from 5 to 500. The zeolites are used in their proton form and may or may not be promoted with metals by ion exchange or impregnation. In addition, the binder used during formulation can have an effect on the yield and product slate.

The oligomerization process can be performed as a single step process or a two-step process. In a single step process, all of the oligomerization is performed in a single stage or in a single reactor in the oligomerization reactor 112. The oligomerization feed stream 110 is introduced into the single stage generally as a gas phase feed. The oligomerization feed stream 110 is contacted with the homogenous catalyst 114 under effective oligomerization conditions. A solvent, such as hexane, cyclohexane, or toluene, may be used for the oligomerization process, and recycled. The ethylene feed may be contacted with the homogenous catalyst 114 at a temperature of 20° C. to 300° C. In some examples, the reaction temperature is at least 25° C., or at least 50° C., or at least 100° C., and is 250° C. or less, or 225° C. or less. The total pressure can be from 1 atm (100 kPa) to 200 atm (20.2 MPa). In some examples, the total pressure is 100 atm (10.1 MPa) or less. In some examples, the oligomerization feed is contacted with the catalyst at a hydrogen partial pressure that is at least 1% of the total pressure, such as at least 5% of the total pressure or at least 10% of the total pressure or up to about 50% on a volumetric basis. The reaction forms a raw oligomer stream 116 that can then be fractionated in a distillation column 118. An optional step of to quench the catalyst may be used, which consists of using a base, either aqueous or organic, before the fractionation.

In the distillation column 118, three streams may be separated from the raw oligomer stream 116. These may include a light olefinic stream 120, an intermediate olefinic stream 122 and a heavy olefinic stream 124. It may be noted that the olefinic streams 120, 122, and 124 may not be composed of 100% olefinic compounds, but may include a number of other compounds, such as paraffin, that are removed in the same boiling point ranges as the olefinic compounds.

The light olefinic stream 120 may include, for example, linear alpha-olefins having from about four carbon atoms to about 10 carbon atoms and unreacted ethylene. Further, as higher molecular weight compounds are formed, the amounts of paraffinic compounds may increase as well. In this example, the light olefinic stream 120 is combined with the oligomerization feed stream 110 and provided to the oligomerization reactor 112 as combined stream 126.

The intermediate olefinic stream 122 may be provided to a dimerization reactor 128. As an example, the intermediate olefinic stream 122 may include compounds having about 12 carbon atoms to compounds having about 22 carbon atoms, although this may be adjusted based, at least in part, on the takeoff point in the distillation column 118. In the dimerization reactor 128, the intermediate olefinic stream 122 may be contacted with a homogeneous or heterogeneous catalyst to be dimerized to form a product that includes carbon compounds having about 24 carbon atoms to about 44 carbon atoms. The reaction may be run at a temperature of about 50° C. to about 400° C., and a pressure of about 50 psig to about 2000 psig. The dimerized stream 130 may be returned to the distillation column 118, in which lower carbon number compounds, such as unreacted compounds having about 12 carbon atoms to about 22 carbon atoms, may be sent back to the dimerization reactor 128 for further processing.

The heavy olefinic stream 124 may have at least about 24 carbon atoms. To lower the amounts of contaminants, as well as to upgrade the final products, the heavy olefinic stream 124 may be provided to a hydro-processing reactor 132 to remove contaminants and improve product properties, such as cold flow properties. For example, hydrotreatment or mild hydrocracking can be used for removal of contaminants, and optionally to provide some viscosity index uplift, while hydrocracking and hydroisomerization, termed catalytic HDC/HDI, may be used to improve cold flow properties.

Hydro-Processing

As used herein, "hydro-processing" includes any hydrocarbon processing that is performed in the presence of hydrogen. The hydrogen may be added to the hydro-processing reactor 132 as a hydrogen treat stream 134. The hydrogen treat stream 134 is fed or injected into a vessel or reaction zone or hydro-processing zone in which the hydroprocessing catalyst is located. The hydrogen treat stream 134 may be pure hydrogen or a hydrogen-containing gas, which is a gas stream containing hydrogen in an amount that is sufficient for the intended reactions. The hydrogen treat stream 134 may include one or more other gasses, such as nitrogen and light hydrocarbons, that do not interfere with or affect either the reactions or the products. Impurities, such as $H_2S$ and $NH_3$ are undesirable and would typically be removed from the hydrogen treat stream 134 before it is conducted to the reactor. The hydrogen treat stream 134 introduced into a reaction stage may include at least 50 vol. % hydrogen or at least 75 vol. % hydrogen. The products of the hydro-processing system 132, termed a hydro-processed stream 136, may have lower contaminants, including metals and heteroatom compounds, as well as improved viscosities, viscosity indices, saturates content, low temperature properties, volatilities and depolarization, and the like.

Various types of hydro-processing can be used in the production of fuels and base stocks, such as hydroconversion, hydrocracking, hydrogenation, hydrotreating, hydrodesulfurization, hydrodenitrogenation, hydrodemetallation, and hydroisomerization, among others. Typical processes include a demetallation process to remove metallic remnants of the catalyst. Further, a catalytic dewaxing, or hydrocracking/hydroisomerization (HDC/HDI) process, may be included to modify viscosity properties or cold flow properties, such as pour point and cloud point. The hydrocracked or dewaxed feed can then be hydrofinished, for example, to saturate olefins and aromatics from the heavy olefinic stream 124. In addition to the above, a hydrotreatment stage can also be used for contaminant removal. The hydrotreatment of the oligomer feed to remove contaminants may be performed prior to or after the hydrocracking or the HDC/HDI.

In the discussion below, a stage in a hydro-processing system 132 can correspond to a single reactor or a plurality of reactors. In some examples, multiple reactors can be used to perform one or more of the processes, or multiple parallel reactors can be used for all processes in a stage. Each stage or reactor may include one or more catalyst beds containing hydro-processing catalyst. Note that a catalyst bed in the discussion below may refer to a partial physical catalyst bed. For example, a catalyst bed within a reactor could be filled partially with a hydrocracking catalyst and partially with an HDC/HDI catalyst. For convenience in description, even though the two catalysts may be stacked together in a single catalyst bed, the hydrocracking catalyst and the HDC/HDI catalyst can each be referred to conceptually as separate catalyst beds. As an example, the hydro-processing system 132 shown in FIG. 1 includes a demetallation system 132A and a hydrocracking/hydroisomerization (HDC/HDI) system 132B, shown as separate reactors or units.

Hydrodemetallation

The demetallation system 132A includes a demetallation catalyst and operates at about 200-500° C. and 50-1200 psi. The demetallation system removes metals in the homogeneous catalyst, such as Fe and Al, from the organic components, which are deposited on the solid catalysts. The demetallation system is typically used for the removal of metals in petroleum oil. The metals in petroleum oil exist as metal complexes, much like the metals in the homogeneous catalysts. The hydrogen treat stream 134 may be added to each of the stages or reactors separately, or may be added in fewer additions, such as to each reactor, or only a first reactor.

Hydroisomerization/Hydrocracking (HDC/HDI)

In the HDC/HDI system 132B, suitable HDC/HDI (dewaxing) catalysts may include molecular sieves such as crystalline aluminosilicates, or zeolites. In various examples, the molecular sieve includes ZSM-5, ZSM-22, ZSM-23, ZSM-35, ZSM-48, SAPO-11, zeolite Beta, or zeolite Y, or includes combinations thereof, such as ZSM-23 and ZSM-48, or ZSM-48 and zeolite Beta. Molecular sieves that are selective for dewaxing by isomerization, as opposed to cracking, may be used, such as ZSM-48, ZSM-23, SAPO-11 or any combinations thereof. The molecular sieves may include a 10-member ring 1-D molecular sieve. Examples include EU-1, ZSM-35 (or ferrierite), ZSM-11, ZSM-57, NU-87, SAPO-11, ZSM-48, ZSM-23, and ZSM-22. Some of these materials may be more efficient, such as EU-2, EU-11, ZBM-30, ZSM-48, or ZSM-23. Note that a zeolite having the ZSM-23 structure with a silica to alumina ratio of from 20:1 to 40:1 may be referred to as SSZ-32. Other molecular sieves that are isostructural with the above materials include Theta-I, NU-10, EU-13, KZ-1, and NU-23. The HDC/HDI catalyst may include a binder for the molecular sieve, such as alumina, titania, silica, silica-alumina, zirconia, or a combination thereof, for example alumina and titania or silica and zirconia, titania, or both.

In various examples, the catalysts may include a hydrogenation catalyst to saturate multiple bonds and aromatics, which may be termed hydrofinishing herein. The hydrogenation catalyst typically includes a metal hydrogenation component that is a Group VI and/or a Group VIII metal. In some examples, the metal hydrogenation component is a Group VIII noble metal. For example, the metal hydrogenation component may be Pt, Pd, or a mixture thereof. Further, the metal hydrogenation component may be a combination of a non-noble Group VIII metal with a Group VI metal. Suitable combinations can include Ni, Co, or Fe with Mo or W, or, in some examples, Ni with Mo or W.

The metal hydrogenation component may be added to the catalyst in any convenient manner. For example, the metal hydrogenation component may be combined with the catalyst using an incipient wetness. In this technique, after combining a zeolite and a binder, the combined zeolite and binder can be extruded into catalyst particles. These catalyst particles may then be exposed to a solution containing a suitable metal precursor. In some examples, metal can be added to the catalyst by ion exchange, where a metal precursor is added to a mixture of zeolite (or zeolite and binder) prior to extrusion.

The amount of metal in the catalyst may be at least about 0.1 wt. % based on catalyst, or at least about 0.15 wt. %, or at least about 0.2 wt. %, or at least about 0.25 wt. %, or at least about 0.3 wt. %, or at least about 0.5 wt. % based on catalyst. The amount of metal in the catalyst may be about 20 wt. % or less based on catalyst, or about 10 wt. % or less, or about 5 wt. % or less, or about 2.5 wt. % or less, or about 1 wt. % or less. For examples where the metal is Pt, Pd, another Group VIII noble metal, or a combination thereof, the amount of metal may be from about 0.1 to about 5 wt. %, about 0.1 to about 2 wt. %, or about 0.25 to about 1.8 wt. %, or about 0.4 to about 1.5 wt. %. For examples where the metal is a combination of a non-noble Group VIII metal with a Group VI metal, the combined amount of metal may be from about 0.5 wt. % to about 20 wt. %, or about 1 wt. % to about 15 wt. %, or about 2.5 wt. % to about 10 wt. %.

The HDC/HDI catalysts may also include a binder. In some examples, the HDC/HDI catalysts may use a low surface area binder. A low surface area binder represents a binder with a surface area of about 100 m²/g or less, or 80 m²/g or less, or about 70 m²/g or less. The amount of zeolite in a catalyst formulated using a binder can be from about 30 wt. % zeolite to about 90 wt. % zeolite relative to the combined weight of binder and zeolite. In some examples, the amount of zeolite may be at least about 50 wt. % of the combined weight of zeolite and binder, such as at least about 60 wt. % or from about 65 wt. % to about 80 wt. %.

A zeolite can be combined with binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture.

Process conditions in a catalytic HDC/HDI zone in a may include a temperature of from about 200 to about 450° C., or from about 270 to about 400° C., a hydrogen partial pressure of from about 1.8 MPag to about 34.6 MPag (about 250 psig to about 5000 psig), or from about 4.8 MPag to about 20.8 MPag, and a hydrogen circulation rate of from about 35.6 m³/m³ (200 standard cubic feet of treat gas per barrel of oil. (SCF/B)) to about 1781 m³/m³ (10,000 SCF/B), or from about 178 m³/m³ (1000 SCF/B) to about 890.6 m³/m³ (5000 SCF/B). In other examples, the conditions can include temperatures in the range of about 343° C. (600° F.) to about 435° C. (815° F.), hydrogen partial pressures of from about 3.5 MPag-20.9 MPag (about 500 psig to 3000 psig), and hydrogen treat gas rates of from about 213 m³/m³ to about 1068 m³/m³ (1200 SCF/B to 6000 SCF/B). These latter conditions may be suitable, for example, if the HDC/HDI stage is operating under sour conditions, e.g., in the presence of high concentrations of sulfur compounds.

The liquid hourly space velocity (LHSV) can vary depending on the ratio of hydrocracking catalyst used to hydroisomerization catalyst in the HDC/HDI catalyst. Relative to the combined amount of hydrocracking and hydroisomerization catalyst, the LHSV may be from about 0.2 h⁻¹ to about 10 h⁻¹, such as from about 0.5 h⁻¹ to about 5 h⁻¹ and/or from about 1 h⁻¹ to about 4 h⁻¹. Depending on the ratio of hydrocracking catalyst to hydroisomerization catalyst used, the LHSV relative to only the HDC/HDI catalyst can be from about 0.25 h⁻¹ to about 50 h⁻¹, such as from about 0.5 h⁻¹ to about 20 h⁻¹, or from about 1.0 h⁻¹ to about 4.0 h⁻¹.

Hydrotreatment Conditions

Hydrotreatment may be used to reduce the sulfur, nitrogen, and aromatic content of the heavy olefinic stream 124, for example, removing nitrogen compounds from the oligomerization catalyst. The catalysts used for hydrotreatment may include hydro-processing catalysts that include at least one Group VIII non-noble metal (Columns 8-10 of IUPAC periodic table), such as Fe, Co, or Ni, or Co or Ni, and at least one Group VI metal (Column 6 of IUPAC periodic table), such as Mo or W. Such hydro-processing catalysts may include transition metal sulfides that are impregnated or dispersed on a refractory support or carrier such as alumina or silica. The support or carrier itself typically has no significant or measurable catalytic activity. Substantially carrier- or support-free catalysts, commonly referred to as bulk catalysts, generally have higher volumetric activities than their bound counterparts.

In addition to alumina or silica, other suitable support or carrier materials can include, but are not limited to, zeolites, titania, silica-titania, and titania-alumina. Suitable aluminas include porous aluminas, such as gamma or eta forms, having average pore sizes from about 50 to about 200 Angstrom (Å), or about 75 to about 150 Å; a surface area from about 100 to about 300 m²/g, or about 150 to about 250 m²/g; and a pore volume of from about 0.25 to about 1.0 cm³/g, or about 0.35 to about 0.8 cm³/g. Generally, any convenient size, shape, or pore size distribution for a catalyst suitable for hydrotreatment of a distillate (including lubricant base oil) boiling range feed in a conventional manner may be used. Further, more than one type of hydro-processing catalyst can be used in one or multiple reaction vessels. A Group VIII non-noble metal, in oxide form, may be present in an amount ranging from about 2 wt. % to about 40 wt. %, or from about 4 wt. % to about 15 wt. %. A Group VI metal, in oxide form, can typically be present in an amount ranging from about 2 wt. % to about 70 wt. %, or, for bound catalysts, from about 6 wt. % to about 40 wt. % or from about 10 wt. % to about 30 wt. %. These weight percentages are based on the total weight of the catalyst. Suitable metal catalysts include cobalt/molybdenum (for example, including about 1-10% Co as oxide and about 10-40% Mo as oxide), nickel/molybdenum (including about 1-10% Ni as oxide and about 10-40% Co as oxide), or nickel/tungsten (including about 1-10% Ni as oxide and about 10-40% W as oxide) on alumina, silica, silica-alumina, or titania, among others.

Hydrotreating conditions can include temperatures of about 200° C. to about 450° C., or about 315° C. to about 425° C.; pressures of about 250 psig (1.8 MPag) to about 5000 psig (34.6 MPag) or about 300 psig (2.1 MPag) to about 3000 psig (20.8 MPag); liquid hourly space velocities (LHSV) of about 0.1 hr⁻¹ to about 10 hr⁻¹; and hydrogen treat rates of about 200 SCF/B (35.6 m³/m³) to 10,000 SCF/B (1781 m³/m³) or about 500 (89 m³/m³) to about 10,000 SCF/B (1781 m³/m³) or about 3000 psig (3.5 MPag-20.9 MPag), and hydrogen treat gas rates of from about 213 m³/m³ to about 1068 m³/m³ (1200 SCF/B 6000 SCF/B).

Hydrofinishing and Aromatic Saturation Process

In some examples, a hydrofinishing stage, an aromatic saturation stage, or both may be used. These stages are termed finishing processes herein. Finishing processes may improve color and stability in a final product by lowering the amounts of unsaturated or oxygenated compounds in the final product streams. The finishing may be performed in the hydro-processing system 132 after the last hydrocracking or hydroisomerization stage. Further, the finishing may occur after fractionation of a hydro-processed stream 136 in a product distillation column 138. If finishing occurs after fractionation, the finishing may be performed on one or more portions of the fractionated product. In some examples, the entire effluent from the last hydrocracking or HDC/HDI process can be finished prior to fractionation into individual product streams.

In some situations, the finishing processes, including hydrofinishing and aromatic saturation, may refer to a single process performed using the same catalyst. Alternatively, one type of catalyst or catalyst system can be provided to perform aromatic saturation, while a second catalyst or catalyst system can be used for hydrofinishing. Typically the finishing processes will be performed in a separate reactor from the HDC/HDI or hydrocracking processes to facilitate the use of a lower temperature for the finishing processes. However, an additional hydrofinishing reactor following a hydrocracking or HDC/HDI process, but prior to fractionation, may still be considered part of a second stage of a reaction system conceptually.

Finishing catalysts can include catalysts containing Group VI metals, Group VIII metals, and mixtures thereof. In an example, the metals may include a metal sulfide compound having a strong hydrogenation function. The finishing catalysts may include a Group VIII noble metal, such as Pt, Pd, or a combination thereof. The mixture of metals may also be present as bulk metal catalysts wherein the amount of metal is 30 wt. % or greater based on the catalyst. The metals and metal compounds may be bound, for example, on a metal oxide. Suitable metal oxide supports include low acidic oxides such as silica, alumina, silica-aluminas or titania, or, in some examples, alumina.

The catalysts for aromatic saturation may include at least one metal having relatively strong hydrogenation function on a porous support. Typical binding materials include amorphous or crystalline oxide materials such as alumina, silica, and silica-alumina. The binding materials may also be modified, such as by halogenation or fluorination. The metal content of the catalyst may be as high as 20 wt. % for non-noble metals. In an example, a hydrofinishing catalyst may include a crystalline material belonging to the M41S class or family of catalysts. The M41S family of catalysts are mesoporous materials having high silica content. Examples include MCM-41, MCM-48 and MCM-50. Examples include MCM-41, MCM-48, MCM-49, and MCM-50. Other catalysts that may be used include Beta, Y, and other large pore zeolites (12-member ring MR and up). If separate catalysts are used for aromatic saturation and hydrofinishing, an aromatic saturation catalyst can be selected based on activity or selectivity for aromatic saturation, while a hydrofinishing catalyst can be selected based on activity for improving product specifications, such as product color and polynuclear aromatic reduction.

Hydrofinishing conditions can include temperatures from about 125° C. to about 425° C., or about 180° C. to about 280° C., a hydrogen partial pressure from about 500 psig (3.4 MPa) to about 3000 psig (20.7 MPa), or about 1500 psig (10.3 MPa) to about 2500 psig (17.2 MPa), and an LHSV from about 0.1 $hr^{-1}$ to about $5^{hr-1}$ LHSV, or, in some examples, 0.5 $hr^{-1}$ to 1.5 $hr^{-1}$. Additionally, a hydrogen treat gas rate of from about 35.6 $m^3/m^3$ to about 1781 $m^3/m^3$ (200 SCF/B to 10,000 SCF/B) can be used.

Fractionation and Products

After hydro-processing, the hydro-processed oligomers in the hydro-processed stream 136 can be fractionated in the product distillation column 138. Any number of fractions may be isolated, including, for example, a distillate stream 140 that may include hydrocarbon fluids, such as gasoline, naphtha, diesel, or a distillate fuel fraction, among others. Fractions that form base stocks for lubricants and other hydrocarbon products, may be isolated, including, for example, a light neutral stream 142, a medium neutral stream 144, and a heavy neutral stream 146. A bottoms stream 148 may also be isolated. In some examples, the bottoms stream 148 may be returned to the hydro-processing reactor 132 for further processing.

Figure 1B:
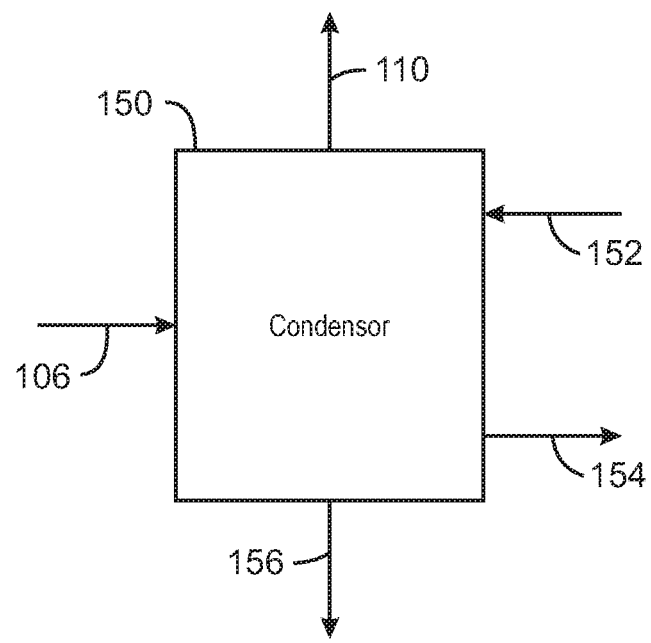
FIG. 1(B) is a simplified block diagram of a recovery system for purifying an impure ethylene stream formed from the dehydration of ethanol, in accordance with examples.

FIG. 1(B) is a simplified block diagram of a separation system 108 for purifying an impure ethylene stream formed from the dehydration of ethanol, in accordance with examples. Like numbered items are as described with respect to FIG. 1. The separation system 108 may be as simple as a condenser 150. In this arrangement, the raw ethylene stream 106, including ethylene, water from the initial azeotropic mixture, and water from the dehydration process, is fed to the condenser 150. A coolant-in stream 152 may include water from a cooling tower, or lower temperature coolants for enhanced removal of water. A coolant-out stream 154 may return the coolant, warmed by condensing water, to a coolant system. The condensed water may be removed in a water stream 156, while the ethylene in the oligomerization feed stream 110 exits through a different port on the vessel and is provided to downstream processing units, such as the oligomerization reactor 112. As described herein, other water removal systems may be used, such as flash tanks, caustic systems, absorption systems, and the like. In some examples, the purification system may remove other compounds, such as sulfur compounds and nitrogen compounds, lowering poison concentrations before the oligomerization process.

Figure 2:
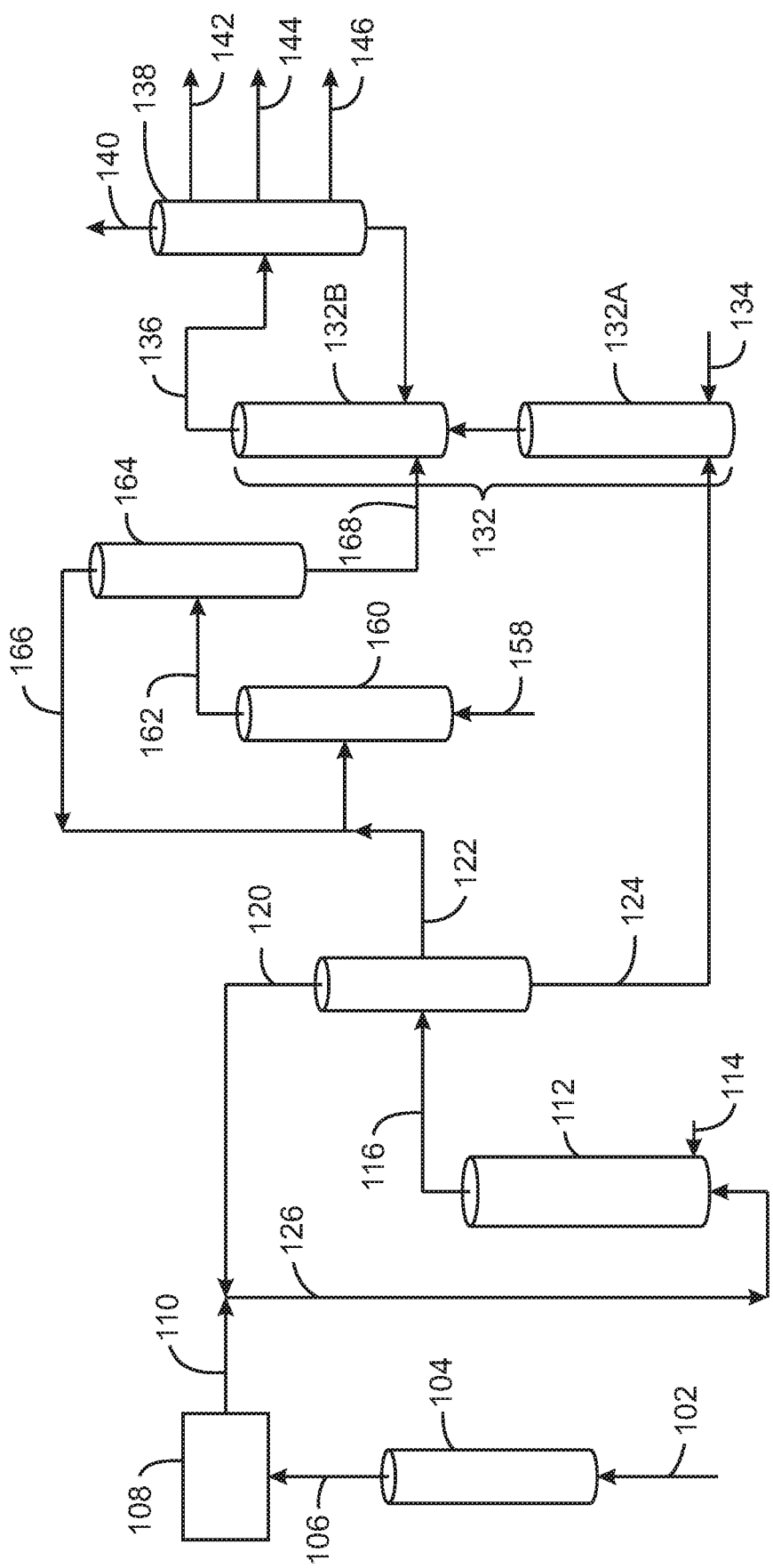
FIG. 2 is a simplified block diagram of another system for producing base stocks from an ethanol feedstock, in accordance with examples.

FIG. 2 is a simplified block diagram of another system 200 for producing base stocks from an ethanol feedstock, in accordance with examples. Like numbered items are as described with respect to FIGS. 1(A) and 1(B). The intermediate olefinic stream 122 is not limited to being upgraded by dimerization, but may be upgraded by other processes, such as alkylation.

As used herein, "alkylation" refers to a process in which a feed stream containing olefins, such the intermediate olefinic stream 122, is reacted with another stream containing hydrocarbons, such as a mixed xylene stream 158, among others, in an alkylation reactor 160. The process converts at least a portion of the olefinic compounds to higher molecular compounds. The alkylation reactor 160 may react the feed streams 122 and 158 in the presence of an acidic catalyst, such as sulfuric acid or hydrofluoric acid, or a solid acid, such as a zeolite, for example zeolite Y, zeolite beta, and zeolite of the MWW family, among others. The alkylation may be run at a temperature of about 50° C. to about 300° C., and a pressure of about 150 psig to about 1000 psig. The process provides an alkylated stream 162 that may be processed in subsidiary units of the alkylation reactor 160 to remove acid and other contaminants before being provided to a separation or distillation column 164.

In the distillation column 164, light or unreacted compounds may be separated into an unreacted stream 166 and blended with the intermediate olefinic stream 122 to be fed back into the alkylation reactor 160. A heavy product stream 168 may be separated out and provided to the HDC/HDI reactor 132B.

Figure 3:
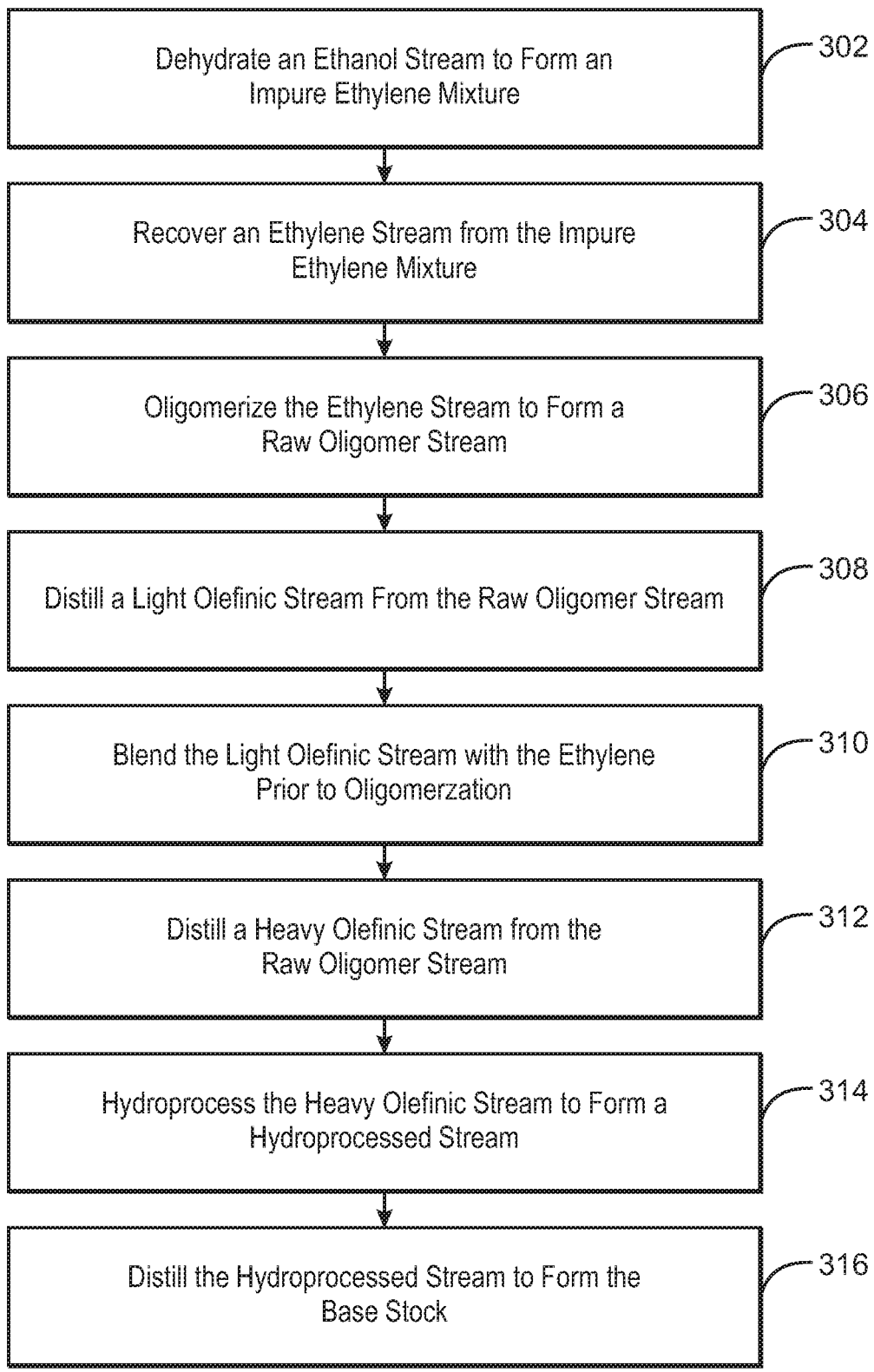
FIG. 3 is a process flow diagram of a method for producing base stocks from an ethanol feedstock, in accordance with examples.

FIG. 3 is a process flow diagram of a method 300 for producing base stocks from an ethanol feedstock, in accordance with examples. The method 300 begins at block 302, with the dehydration of an ethanol stream to form an impure ethylene mixture. As described herein, the impure ethylene mixture may include ethylene, water, and low amounts of other contaminants, depending on the purification process for the ethanol stream.

At block 304, an ethylene stream may be recovered from the impure ethylene mixture. This may be performed by passing the impure ethylene stream through a condenser to remove water from the impure ethylene stream. Other actions may be performed for the purification, including, for example, passing the output stream from the condenser through a coldbox to remove any remaining traces of water or other contaminants.

At block 306, the ethylene stream may be oligomerized to form a raw oligomer stream. As described herein, this may be performed by contacting the ethylene stream with a homogeneous catalyst to form the raw oligomer stream, wherein the raw oligomer stream may have a substantial concentration of linear alpha olefins.

At block 308, a light olefinic stream may be distilled from the raw oligomer stream. The light olefinic stream may include compounds having between about four and about 12 carbons. At block 310 the light olefinic stream is blended with the ethylene stream prior to oligomerization. As noted herein, an olefinic stream may not include 100% olefinic compounds, but may include other compounds, such as paraffinic compounds, that have a similar boiling point to the olefinic compounds.

At block 312, a heavy olefinic stream is distilled from the intermediate stream. At block 314, the heavy olefinic stream is hydro-processed to form a hydro-processed stream. In the hydro-processing, the heavy olefinic stream may be hydrodemetallated to remove any traces of catalyst remaining from the oligomerization. The heavy olefinic stream may then be hydrocracked to form lower molecular weight compounds, for example, having a broader distribution. The heavy olefinic stream may be hydroisomerized to form a distribution of different isomers. Further, the heavy olefinic stream may be finished to decrease unsaturated and aromatic compounds in the hydro-processed stream.

At block 316, the hydro-processed stream is distilled to form the base stock. Distilling the hydro-processed stream may include separating a distillate stream, a naphtha stream, or both from the hydro-processed stream. Further, distilling the hydro-processed stream may include forming a heavy neutral oil stock stream, a medium neutral oil stock stream, or a light neutral oil stock stream, or any combinations thereof.

The method may include more or fewer steps than described with respect to FIG. 3. For example, an intermediate olefinic stream, including compounds having between about 12 and about 22 carbon atoms, may be distilled from the raw oligomer stream and upgraded in molecular weight. As described with respect to FIGS. 1 and 2, this may be performed by dimerization or alkylation.

EXAMPLES

Example 1: Linear Alpha Olefins of Different Schulz-Flory Molecular Distribution may be Produced from Ethylene using a Homogeneous Catalyst The molecular distribution may be controlled by the catalyst, for example, through the ligands. FIG. 4 is a drawing 400 of related homogeneous catalysts, having different ligands, that may be used for the oligomerization or dimerization processes, in accordance with examples. The catalysts are labeled A-D, and are described further with respect to the oligomerization reactions. Catalyst E may be used in the dimerization process.

The tests of the catalysts in the oligomerization process were performed in a 500 milliliter (mL) autoclave. A 100 mL toluene solution containing 20 micromoles (μmol) catalyst and 4000 μmol MAO activator was charged to the autoclave. Then a predetermined amount of $N_2$, or a mixture of $H_2$ and $N_2$ in some examples, as described with respect to Tables 1-3, was charged into the autoclave to bring the autoclave to a preset pressure. The autoclave was then heated to 50° C. before ethylene was introduced. The reaction was exothermic and ethylene addition was controlled to keep the temperature below about 120° C. and a final total pressure of about 400 psi. The oligomerization reaction was allowed to proceed for approximately 30 minutes.

The autoclave was then cooled to room temperature and overhead gas pressure was released via opening of a valve. The reaction product, in the form of a solution or suspension was then recovered, quenched with an aqueous HCl solution, and the aqueous phase containing Fe and Al was discarded. The reaction product was analyzed via gas chromatography (GC) and nuclear magnetic resonance (NMR) techniques.

The gas chromatography analysis for ethylene oligomers was performed using method to enable coverage up to C30. The column was 30 m long, with an inner diameter of 0.32 millimeters and a packing of 0.25 μm, available as a HP-5 column from Agilent. The carrier gas was nitrogen. The injector was held at a temperature of 150° C. and 10 psi. A 50 to 1 split ratio was used with a 121 mL per minute (mL/min) total flow rate and an injection size of 1-5 μL. The column oven was set to a 50° C. initial temp with a 10° C./min ramp rate to a 320° C. final temperature. It was held at the 320° C. temperature for 8 minutes giving a total run time of 35 minutes. The detector was a flame ionization detector held at 300° C., using a 30 mL/min flow of hydrogen, a 250 mL/min flow of air, and a 25 mL/min makeup stream of nitrogen. The gas chromatography analysis for dimerization or alkylation products was performed using a high temperature method to enable coverage up to C100. The column was 6 m long, with an inner diameter of 0.53 millimeters and a packing of 0.15 μm, available as a MXT-1 SimDist column from Restek company of State College, Pa. The carrier gas was nitrogen. The injector was held at a temperature of 300° C. and 0.9 psi. A 15 to 1 split ratio was used with a 27.4 mL per minute (mL/min) total flow rate and an injection size of 1 μL. The column oven was set to an 80° C. initial temp with a 15° C./min ramp rate to a 400° C. final temperature. It was held at the 400° C. temperature for 15 minutes giving a total run time of 36.3 minutes. The detector was a flame ionization detector held at 300° C., using a 40 mL/min flow of hydrogen, a 200 mL/min flow of air, and a 45 mL/min makeup stream of nitrogen.

Another gas chromatography analysis was performed using a high temperature method to enable coverage up to C100. The column was 6 m long, with an inner diameter of 0.53 millimeters and a packing of 0.15 μm, available as a MXT-1 SimDist column from Restek company of State College, Pa. The carrier gas was nitrogen. The injector was held at a temperature of 300° C. and 0.9 psi. A 15 to 1 split ratio was used with a 27.4 mL per minute (mL/min). Total flow rate and an injection size of 1 μL. The column oven was set to an 80° C. initial temp with a 15° C./min ramp rate to a 400° C. final temperature. It was held at the 400° C. temperature for 15 minutes giving a total run time of 36.3 minutes. The detector was a flame ionization detector held at 300° C., using a 40 mL/min flow of hydrogen, a 200 mL/min flow of air, and a 45 mL/min makeup stream of nitrogen.

The C-13 NMR analysis was performed using a Bruker 400 MHz Advance III spectrophotometer. The samples were dissolved in chloroform-D ($CDCl_3$) or toluene-D8 in a 5 mm NMR tube at concentrations of between 10 to 15 wt. % prior to being inserted into the spectrophotometer. The C-13 NMR data was collected at room temperature (20° C.). The spectra were acquired with time averaging to provide a signal to noise level adequate to measure the signals of interest. Prior to data analysis, spectra were referenced by setting the chemical shift of the $CDCl_3$ solvent signal to 77.0 ppm.

H-1 NMR data was collected at room temperature. The data was recorded using a maximum pulse width of 45 degree, 8 seconds between pulses and signal averaging of 120 transients.

The analyses confirmed that the products were mostly linear alpha-olefins (LAOs) having Schulz-Flory (S-F) distributions. The S-F distribution constant, u, was determined by an average of the molar ratios of C16/C14; C14/C12; and C12/C10 in the product, as determined by gas chromatography.

The information in Table 1 shows the basic comparison between oligomerizations performed using catalysts A-D. For these runs, the reaction conditions included about 200 psi or ethylene, about 200 psi of hydrogen, a reaction temperature of about 80° C. to 100° C., 100 mL of toluene (as a catalyst solvent), 20 µmol of catalyst, and a ratio of 200 mol/mol of activator (co-catalyst) to catalyst, such as the MAO activators described herein.

TABLE 1

Comparison of oligomerization by catalyst A-D

| Example | Catalyst | Alpha Value | % Linear Alpha Olefin* | % Branched Olefins* | % Linear Paraffin* |
|---|---|---|---|---|---|
| X1 | A | 0.339 | 66.6 | 22.1 | 1.6 |
| X2 | B | 0.667 | 92.9 | 5.2 | 1.2 |
| X3 | C | 0.828 | 96.0 | 1.1 | 2.4 |
| X4 | D | 0.947 | 34.5 | 0.2 | 64.7 |

*Presented in C12 fraction as determined by gas chromatography and mass spectrometry Catalyst B was chosen to determine the effects of changing the ratio of hydrogen to nitrogen on the reaction. The results are shown in Table 2. For these runs, the reaction conditions included about 200 psi or ethylene, about 200 psi of hydrogen or a mixture of hydrogen and nitrogen, a reaction temperature of about 80° C. to 100° C., 100 mL of toluene, 20 µmol of catalyst, and a ratio of 200 mol/mol of activator (co-catalyst) to catalyst. As can be seen by the results in Table 2, changing the hydrogen to nitrogen ratio has relatively small effects on the operation of the catalyst.

TABLE 2 comparison of oligomerization under changing ratios of hydrogen and nitrogen using catalyst B

| Example | Catalyst | H2/N2, psi | Alpha Value | % Linear Alpha Olefin* | % Branched Olefins* | % Linear Paraffin* |
|---|---|---|---|---|---|---|
| X2 | B | 200/0 | 0.667 | 92.9 | 5.2 | 1.2 |
| X5 | B | 20/180 | 0.666 | 92.2 | 6.3 | 0.8 |
| X6 | B | 2/198 | 0.698 | 89.2 | 8.6 | 1.1 |

*Presented in C12 fraction as determined by gas chromatography and mass spectrometry Catalyst C was chosen to determine the effects of changing the solvent for the reaction. The results are shown in Table 3. For these runs, the reaction conditions included about 200 psi or ethylene, about 200 psi of hydrogen or a mixture of hydrogen and nitrogen, a reaction temperature of about 80 to 100° C., 100 mL of a solvent as identified in Table 3, 20-40 µmol of catalyst, and a ratio of 100-200 mol/mol of activator (co-catalyst) to catalyst.

TABLE 3 comparison of oligomerization using different solvents and catalyst C

| Example | Catalyst | Solvent | Alpha Value | % Linear Alpha Olefin* | % Branched Olefins* | % Linear Paraffin* |
|---|---|---|---|---|---|---|
| X3 | C | Toluene | 0.828 | 96.0 | 1.1 | 2.4 |
| X7 | C | Isohexane | 0.825 | 92.2 | 1.28 | 3.7 |
| X8 | C | Cyclohexane | 0.826 | 91.4 | 1.87 | 3.9 |

*Presented in C12 fraction as determined by gas chromatography and mass spectrometry The results of the runs in Tables 1-3 indicate that controlling the ligands of the catalyst may be used to control both the paraffin/olefin ratio and the S-F distribution product composition. It may also be noted that the oligomerization using catalysts A-D is tolerant of a large amount of $H_2$ and a variety of solvents.

Figure 5:
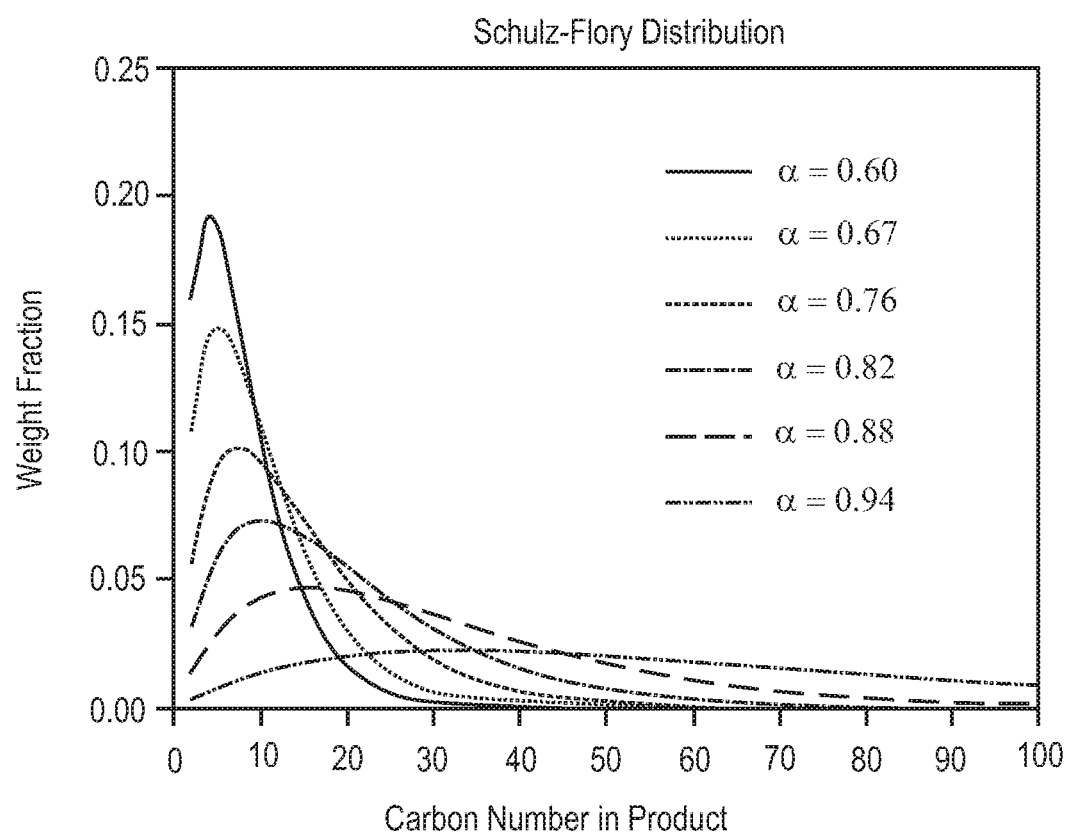
FIG. 5 is a plot of the Schultz-Flory distribution of a product that includes different carbon numbers, in accordance with examples.

FIG. 5 is a plot 500 of the Schultz-Flory distribution of a product that includes different carbon numbers, in accordance with examples. The weight fraction of the Schulz-Flory product distribution with experimentally obtained a values may be plotted against the carbon number in the product. The same data can be recast to show lumped fraction distribution as a function of a value.

Figure 6:
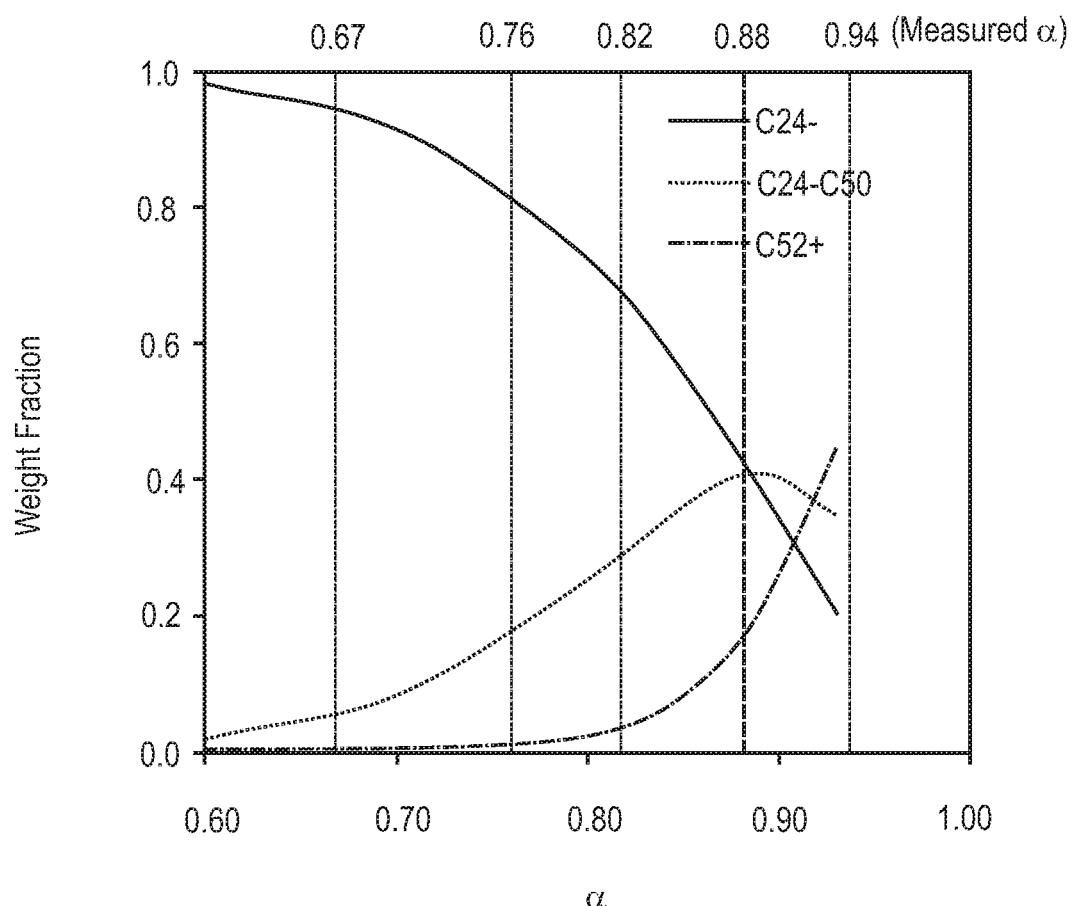
FIG. 6 is a plot of the effect of the change in carbon number composition on a weight fraction of a product as the Schultz-Flory distribution changes, in accordance with examples.

FIG. 6 is a plot 600 of the effect of the change in carbon number composition on a weight fraction of a product as the Schultz-Flory distribution changes, in accordance with examples. The plot 600 shows C24−, C24-C50, and C52+ fractions as a function of a value, indicating that the lube molecule range C24-C50 has a maximum value of about 40 wt. % at an a value around 0.88. This further illustrates that the lube/LAO split may be effectively controlled by using different catalysts that offer different a values.

Example 2: Dimerizing an Intermediate Olefinic Stream (C14-C24) into Lube Range Molecules The dimerization may be performed by either heterogeneous catalysts, such as solid acid catalysts, or homogeneous organometallic catalysts. For example, solid acids include proton form zeolite, acid treated clay, amorphous silica-alumina, acid form ion-exchange resins, and various $WO_3/ZrO_2$ mixed metal oxides.

To test the dimerization, a 19-g mixture of C14-C24 linear alpha olefins was treated with 200 mg of Catalyst E and 1 mL of MAO (30% Al) at room temperature overnight. The resulting mixture was diluted with hexane and then hydrolyzed with aqueous HCl.

FIGS. 7(A) and 7(B) are plots of gas chromatograms illustrating the changes caused by dimerization 702 of the alpha olefin mixture, in accordance with examples. The plots 700 are of the starting material 704 and the product 706. The plot of the starting material 704 shows a first set of peaks 708 from the C14-C24 linear alpha-olefins (LAOs) generated by a homogeneous catalyst, such as catalyst E.

After dimerization, a second set of peaks 710 show a significant decrease in the amount of C14-C24 LAOs, as well as some broadening, indicating reaction of the LAOs. A new set of peaks 712 is present after the reaction, corresponding to C26 to C52 (and higher) olefins. This illustrates the effectiveness of dimerization in increasing the molecular weight of the LAOs. Other techniques, such as alkylation, may be used to increase the molecular weight of the LAOs.

Example 3: Hydroisomerizing Lube Range Olefin Molecules to Lube Oil

The hydroisomerization of olefins may broaden the molecular weight distributions of the olefins, improving characteristics such as pour point, VI, and others. This may be performed by a number of acid catalysts, such as the ZSM-48 catalyst described in the synthesis procedure below.

Preparation of Formulated ZSM-48 Catalyst

To form a bound ZSM-48 catalyst, 65 parts ZSM-48 zeolite crystals are combined with 35 parts pseudoboehmite alumina dry powder, on a calcined dry weight basis. The ZSM-48 and the pseudoboehmite alumina dry powder are placed in a muller or a mixer and mixed for about 10 to 30 minutes. Sufficient water is added to the ZSM-48 and alumina during the mixing process to produce an extrudable paste.

The extrudable paste is formed into a 1/16 inch quadralobe extrudate using an extruder. After extrusion, the 1/16th inch quadralobe extrudate is dried at a temperature ranging from about 250° F. (about 120° C.) to about 325° F. (about 163° C.). After drying, the dried extrudate is heated to about 1000° F. (about 538° C.) under flowing nitrogen. The extrudate is then cooled to ambient temperature and humidified with saturated air or steam. After the humidification, the extrudate is ion exchanged with about 0.5 to about 1 N ammonium nitrate solution. The ammonium nitrate solution ion exchange is repeated. The ammonium nitrate exchanged extrudate is then washed with deionized water to remove residual nitrate prior to calcination in air. After washing the wet extrudate, it is dried. The exchanged and dried extrudate is then calcined in a nitrogen/air mixture to about 1000° F. (about 538° C.). Following calcination, the extrudate was exposed to steam at about 700° F. (about 371° C.) for about three hours.

The formulated ZSM-48 catalyst was added to the dimerized product described with respect to FIG. 7(A) in Example 2. The mixture was heated in an closed autoclave at hydroisomerization condition of about 200-250° C. and about 500-1000 psi $H_2$ for 1 to 5 days.

Figures 8A, 8B:
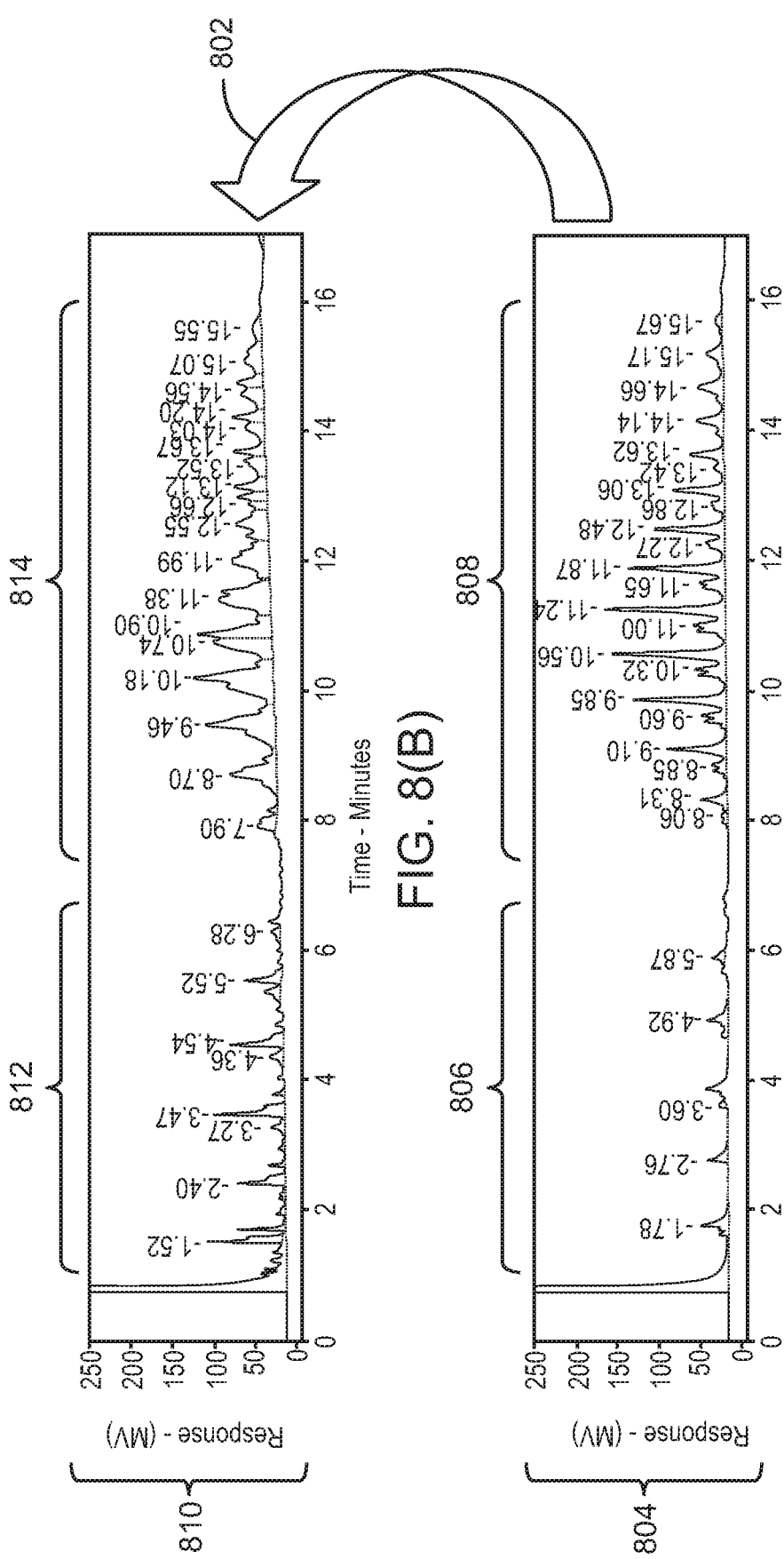
FIGS. 8(A) and 8(B) are plots of gas chromatograms illustrating the changes caused by hydroisomerization of an alpha olefin mixture, in accordance with examples.

FIGS. 8(A) and 8(B) are plots of gas chromatograms illustrating the changes caused by hydroisomerization 802 of an olefin mixture 804, in accordance with examples. As shown in FIG. 8(A), and described with respect to FIG. 7(A), the olefin mixture 804 includes C14-C24 olefins 806 and C28-C52 olefins 808. The gas chromatogram of the reaction products 810, including isomerized C14-C24 812 and isomerized C28-C52 814, is shown in FIG. 8(B). GC traces of the before and after hydroisomerization materials are shown below, which clearly indicate isomerization of the molecules (broadening of peaks).

Figure 9:
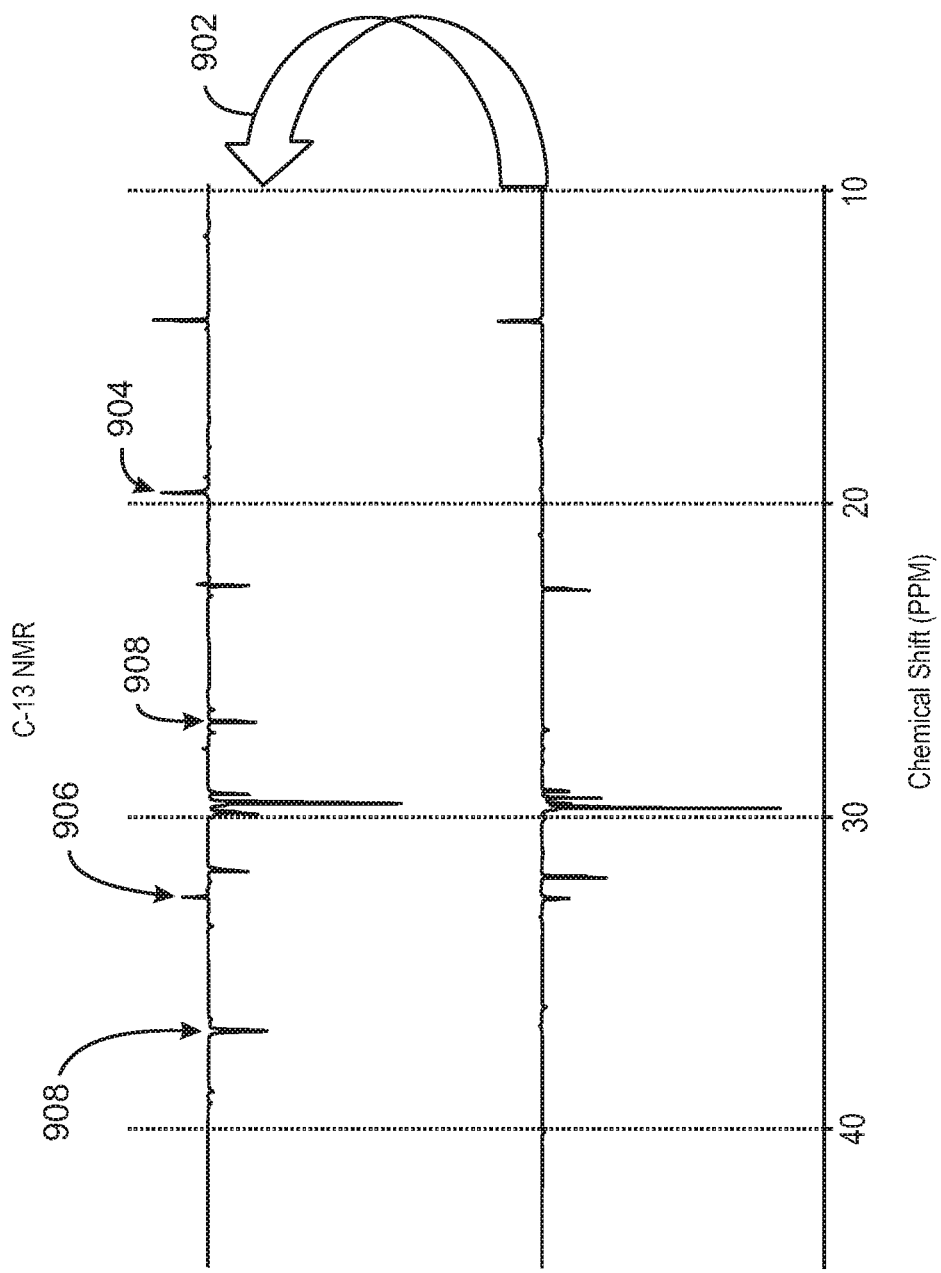
FIG. 9 is a plot of DEPT-135 C-13 NMR spectra illustrating the changes caused by hydroisomerization of an alpha olefin mixture, in accordance with examples.

FIG. 9 is a plot 900 of the DEPT-135 C-13 NMR spectra illustrating the changes caused by hydroisomerization 902 of an alpha olefin mixture, in accordance with examples. As used herein, DEPT is an acronym for distortionless enhancement by polarization transfer. The technique is used to determine the multiplicity of carbon atoms substitution with hydrogen. The DEPT-135 C-13 NMR spectra of the products of hydroisomerization of dimerized C14-C24 LAOs show the presence of isolated methyl (CH3, ~20 ppm) branching 904, and the associated methine (CH, ~32 ppm) carbon 906 and methylene carbons 908 (CH2, ~27 and ~37 ppm) adjacent to the methine (CH) carbon.

TABLE 4

Comparisons of dimerized and hydroisomerized products.

| | Example | | | |
|---|---|---|---|---|
| | X9 | X10 | X11 | X12 |
| | Description | | | |
| | Dimerized C14-C24 LAO | Hydro-isomerized X9 | Dimerized C14 + LAO | Hydro-isomerized X11 |
| Mn by GPC | 412 | 374 | 464 | 405 |
| Mw by GPC | 466 | 437 | 658 | 463 |
| PD by GPC | 1.13 | 1.17 | 1.42 | 1.14 |
| Tm by DSC, ° C. | 25.4 | 6.4 | 47.0 | 30.2 |
| Tg by DSC, ° C. | −16.5 | −66.5 | −5.4 | −25.2 |

In Table 4, Mn is the number averaged molecular weight, Mw is the weight averaged molecular weight, and PD is the polydispersity, calculated as Mw/Mn. The GPC or gel permeation chromatography is calibrated with polyethylene standards. DSC is differential scanning calorimetry. Tm is the melting point or crystallization temperature of the material and Tg is the glass transition temperature of the material.

Example 4: LAO Recycle and Reactions with Ethylene in the Oligomerization Reaction Zone It is also anticipated that the non-lube range LAO can be incorporated into the ethylene oligomers during the oligomerization process. The results of the tests are shown in Table 5. For these runs, the reaction conditions included about 100 or 200 psi or ethylene, about 200 psi of hydrogen, a reaction temperature of about 80 to 100° C., 100 mL of toluene, 20 μmol of catalyst C or E, and a ratio of 100-200 mol/mol of activator (MAO co-catalyst) to catalyst.

This is demonstrated by addition of 1-pentene after introduction of ethylene to the system. The incorporation of 1-pentene is evident in the results shown in Table 5 by the increasing amount of odd number olefins such as tridecenes (C13 olefins) as well as branched isomers within the odd number olefins, which indicates the incorporation of an already formed LAO into a growing LAO chain, causing branching. For Table 5, the S-F distribution constant, a, was determined by averaging the molar ratios: C16/C14; C14/C12; and C12/C10 in the product, as determined by gas chromatography, as described herein.

TABLE 5

Incorporation of 1-pentene into oligomers.

| | | | | | C12 Fraction | | | C13 Fraction | | |
|---|---|---|---|---|---|---|---|---|---|---|
| Example | Catalyst | 1-Pentene added | C2H4/H2, psi | Alpha Value | % in C10-C20** | % Linear Alpha Olefin* | % Branched Olefins* | % in C10-C20** | % Linear Alpha Olefin* | % Branched Olefins* |
| X3  | C | No  | 200/200 | 0.828 | 17.5 | 96.0 | 1.1 | 0.5 | 78.9 | 13.8 |
| X13 | C | Yes | 200/200 | 0.845 | 16.4 | 92.3 | 1.2 | 1.6 | 64.3 | 26.4 |
| X14 | C | Yes | 100/200 | 0.869 | 14.2 | 87.0 | 1.8 | 3.4 | 49.0 | 39.4 |
| X15 | E | No  | 200/200 | 0.678 | 21.7 | 92.9 | 4.2 | 0.5 | 70.8 | 20.7 |
| X16 | E | Yes | 200/200 | 0.741 | 17.9 | 87.1 | 8.5 | 2.9 | 51.2 | 39.3 |

*Presented in C12 or C13 fractions as determined by gas chromatography and mass spectrometry
**Normalized to C10-C20

EMBODIMENTS

The embodiments of the present techniques include any combinations of the examples in the following numbered paragraphs.

1. A system for manufacturing a base stock from an ethanol stream, including a dehydration reactor configured to form an impure ethylene stream from the ethanol stream, a recovery system configured to purify the impure ethylene stream to form an ethylene stream, and an oligomerization reactor configured to oligomerize the ethylene stream to form a raw oligomer stream. The system also includes a distillation column configured to separate the raw oligomer stream into a light olefinic stream, an intermediate olefinic stream, and a heavy olefinic stream, wherein the light olefinic stream is blended with the ethylene stream to form a blended stream, and the blended stream is provided to the oligomerization reactor. A hydro-processing system is configured to hydroprocess the heavy olefinic stream to form a hydroprocessed stream, and a product distillation column is configured to separate the hydroprocessed stream to form the base stock.

2. The system of embodiment 1, including a dimerization reactor configured to dimerize the intermediate olefinic stream and return a dimerized stream to the distillation column.

3. The system of either embodiments 1 or 2, including an alkylation reactor configured to alkylate the intermediate olefinic stream and provide an alkylated stream to an alkylation distillation column.

4. The system of embodiment 3, wherein the alkylation distillation column is configured to separate an unreacted olefin stream from the alkylated stream and return the unreacted olefin stream to the alkylation reactor.

5. The system of any of embodiments 1 to 4, including a bioreactor to generate the ethanol stream.

6. The system of any of embodiments 1 to 5, wherein the dehydration reactor includes a fluidized bed reactor including a heterogeneous catalyst.

7. The system of any of embodiments 1 to 6, wherein the oligomerization reactor is configured to use a homogeneous catalyst.

8. The system of embodiment 7, wherein the homogeneous catalyst includes an iron (II) pyridine-bis-imine (Fe—PBI) catalyst including a structure of

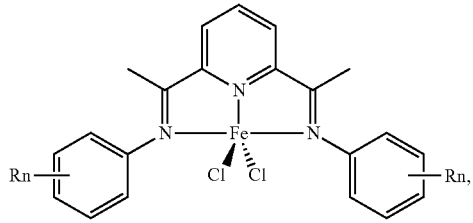

wherein Rn includes one, two, or three substituents, and wherein the substituents include $CH_3$, F, or both.

9. The system of any of embodiments 1 to 8, wherein the hydro-processing system includes a demetallation unit.

10. The system of any of embodiments 1 to 9, wherein the hydro-processing system includes a hydrocracking unit.

11. The system of any of embodiments 1 to 10, wherein the hydro-processing system includes a hydroisomerization unit.

12. The system of any of embodiments 1 to 11, wherein the product distillation column is configured to separate the hydroprocessed stream into a distillate stream including naphtha, a heavy neutral stream, a medium neutral stream, and a light neutral stream.

13. A method for manufacturing a base stock from an ethanol stream, including dehydrating an ethanol stream to form an impure ethylene stream, recovering an ethylene stream from the impure ethylene stream, and oligomerizing the ethylene stream to form a raw oligomer stream. The method also includes distilling a light olefinic stream from the raw oligomer stream and blending the light olefinic stream into the ethylene stream prior to the oligomerization. A heavy olefinic stream is distilled from the raw oligomer stream, and the heavy olefinic stream is hydro-processed to form a hydroprocessed stream. The hydroprocessed stream is distilled to form the base stock.

14. The method of embodiment 13, wherein dehydrating the ethanol stream includes reacting the ethanol stream over an acid catalyst to form ethylene and water.

15. The method of either embodiments 13 or 14, wherein dehydrating the ethanol stream includes reacting the ethanol stream over a zeolite catalyst to form ethylene and water.

16. The method of any of embodiments 13 to 15, including distilling an intermediate olefinic stream from the raw oligomer stream.

17. The method of embodiment 16, including dimerizing the intermediate olefinic stream to form a dimerized stream, and distilling the dimerized stream with the raw oligomer stream.

18. The method of embodiment 16, including alkylating the intermediate olefinic stream to form an alkylated stream, distilling the alkylated stream to form a lights stream and a heavies stream, combining the lights stream with the intermediate olefinic stream to form a combined stream, and alkylating the combined stream.

19. The method of embodiment 18, including hydro-processing the heavies stream.

20. The method of embodiments 13 to 19, wherein oligomerizing the ethylene stream includes contacting the ethylene stream with a homogeneous catalyst including an iron (II) pyridine-bis-imine.

21. The method of embodiments 13 to 20, including separating an unreacted ethylene stream from the raw oligomer stream, and oligomerizing the unreacted ethylene stream with the ethylene stream.

22. The method of embodiments 13 to 21, including distilling a light linear alpha olefin stream from the raw oligomer stream.

23. The method of embodiments 13 to 22, distilling a heavy linear alpha olefin stream from the raw oligomer stream.

24. The method of embodiments 13 to 23, wherein hydro-processing the heavy olefinic stream includes hydrocracking the heavy olefinic stream.

25. The method of embodiments 13 to 24, wherein hydro-processing the heavy olefinic stream includes hydroisomerizing the heavy olefinic stream.

26. The method of embodiments 13 to 25, wherein distilling the hydroprocessed stream includes separating a distillate stream, a naphtha stream, or both from the hydroprocessed stream.

27. The method of embodiments 13 to 26, wherein distilling the hydroprocessed stream includes forming a heavy neutral oil stock stream, a medium neutral oil stock stream, or a light neutral oil stock stream, or any combinations thereof.

28. A system for manufacturing a base oil stock from ethanol, including a dehydration reactor to form an impure ethylene stream from an ethanol stream, a recovery system to form an ethylene stream from the impure ethylene stream, and an oligomerization reactor configured to convert the ethylene stream to a raw olefinic stream by contacting the ethylene stream with a homogeneous catalyst. The system includes a distillation column configured to separate a light olefinic stream and a heavy olefinic stream from the raw olefinic stream and to combine the light olefinic stream into the ethylene stream to the oligomerization reactor. A hydroprocessing reactor is configured to hydroprocess the heavy olefinic stream to form a hydroprocessed stream, and a product distillation column to separate the hydroprocessed stream to form a number of base stock streams.

29. The system of embodiment 28, wherein the distillation column is configured to separate an intermediate olefinic stream from the raw olefinic stream.

30. The system of embodiment 29, including a dimerization reactor configured to dimerize the intermediate olefinic stream to form a dimerized stream and return the dimerized stream to the distillation column.

31. The system of embodiment 29, including an alkylation reactor configured to alkylate the intermediate olefinic stream to form an alkylated stream.

32. The system of embodiment 31, including an alkylation distillation column configured to separate the alkylated stream into a reacted stream and an unreacted stream, and return the unreacted stream to the alkylation reactor.

33. The system of any of embodiments 28 to 32, wherein the homogeneous catalyst includes an iron (II) pyridine-bis-imine (Fe—PBI) compound including a structure of

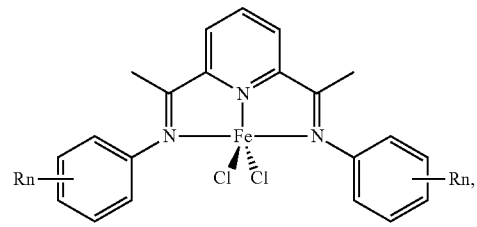

wherein Rn includes one, two, or three substituents, and wherein the substituents include $CH_3$, F, or both.

34. The system of any of embodiments 28 to 33, wherein the hydroprocessed stream is demetallated, hydrocracked, or hydroisomerized, or any combination thereof.

While the present techniques may be susceptible to various modifications and alternative forms, the examples discussed above have been shown only by way of example. However, it should again be understood that the techniques is not intended to be limited to the particular examples disclosed herein. Indeed, the present techniques include all alternatives, modifications, and equivalents falling within the true spirit and scope of the appended claims.

The invention claimed is:

1. A method for manufacturing a base stock from an ethanol stream, comprising:
    dehydrating an ethanol stream to form an impure ethylene stream;
    recovering an ethylene stream from the impure ethylene stream;
    oligomerizing the ethylene stream to form a raw oligomer stream;
    distilling a light olefinic stream, an intermediate olefinic stream and a heavy olefinic stream from the raw oligomer stream and recycling the light olefinic stream to the ethylene stream;
    alkylating the intermediate olefinic stream to form an alkylated stream;
    distilling the alkylated stream to form a lights stream and a heavies stream;
    recycling the lights stream to the intermediate olefinic stream;
    subjecting the heavy olefinic stream to hydrodemetallation to form a first hydroprocessed stream;
    subjecting the first hydroprocessed stream and the heavies stream to hydrocracking and/or hydroisomerization to form a second hydroprocessed stream; and
    distilling the second hydroprocessed stream to form the base stock.

2. The method of claim 1, wherein said dehydrating the ethanol stream comprises reacting the ethanol stream over an acid catalyst to form ethylene and water.

3. The method of claim 1, wherein said dehydrating the ethanol stream comprises reacting the ethanol stream over a zeolite catalyst to form ethylene and water.

4. The method of claim 1, wherein oligomerizing the ethylene stream comprises contacting the ethylene stream with a homogeneous catalyst comprising an iron (II) pyridine-bis-imine.

5. The method of claim 1, comprising:
    separating an unreacted ethylene stream from the raw oligomer stream; and recycling the unreacted ethylene stream to the ethylene stream.

6. The method of claim 1, wherein the light olefinic stream comprises light linear alpha olefins.

7. The method of claim 1, wherein the heavy olefinic stream comprises heavy linear alpha olefins.

8. The method of claim 1, wherein said distilling the second hydroprocessed stream comprises separating a distillate stream, a naphtha stream, or both from the second hydroprocessed stream.

9. The method of claim 1, wherein said distilling the second hydroprocessed stream comprises forming a heavy neutral oil stock stream, a medium neutral oil stock stream, or a light neutral oil stock stream, or any combinations thereof.

* * * * *